United States Patent
Zeiner et al.

(10) Patent No.: US 12,161,331 B2
(45) Date of Patent: Dec. 10, 2024

(54) THERMALLY FORMED TISSUE CUSHION ADJUNCT FOR SURGICAL STAPLER END EFFECTOR

(71) Applicant: Cilag GmbH International, Zug (CH)

(72) Inventors: Mark S. Zeiner, Mason, OH (US); Adam D. Hensel, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/704,082

(22) Filed: Mar. 25, 2022

(65) Prior Publication Data

US 2023/0301657 A1    Sep. 28, 2023

(51) Int. Cl.
*A61B 17/072* (2006.01)
*A61B 17/00* (2006.01)

(52) U.S. Cl.
CPC .. *A61B 17/07292* (2013.01); *A61B 17/07207* (2013.01); *A61B 2017/00893* (2013.01); *A61B 2017/00955* (2013.01); *A61B 2017/07264* (2013.01); *A61B 2017/07271* (2013.01); *A61B 2017/07285* (2013.01)

(58) Field of Classification Search
CPC ........ A61B 17/07292; A61B 17/07207; A61B 2017/07264; A61B 2017/07271; A61B 2017/07285; A61B 18/14; A61B 18/1492; A61B 2018/00577; A61B 2018/00589; A61B 2018/00595; A61B 2018/00601; A61B 2018/00607; A61B 2018/00619; A61B 2018/0063; A61B 2018/1445
See application file for complete search history.

(56) References Cited

U.S. PATENT DOCUMENTS 5,810,855 A * 9/1998 Rayburn .......... A61B 17/07207
                                                          606/220
7,380,696 B2    6/2008 Shelton, IV et al.
(Continued)

FOREIGN PATENT DOCUMENTS

EP    2090248 A2    8/2009
EP    3150134 A1    4/2017
(Continued)

OTHER PUBLICATIONS

International Search Report and Written Opinion dated Aug. 2, 2023, for International Application No. PCT/IB2023/052793, 20 pages.
(Continued)

*Primary Examiner* — Robert F Long
*Assistant Examiner* — Eduardo R Ferrero
(74) *Attorney, Agent, or Firm* — Frost Brown Todd LLP

(57) ABSTRACT

An apparatus configured for use with an end effector of a surgical fastening instrument includes a first adjunct including a plurality of first resiliently compressible elements interconnected with each other. The apparatus also includes a second adjunct opposed from the first adjunct. The second adjunct includes a plurality of second resiliently compressible elements interconnected with each other. Each first resiliently compressible element of the plurality of first resiliently compressible elements is configured to align and thermally bond with a corresponding second resiliently compressible element of the plurality of second resiliently compressible elements to secure the first and second adjuncts to each other.

20 Claims, 19 Drawing Sheets

(56) References Cited

U.S. PATENT DOCUMENTS

| | | |
|---|---|---|
| 7,845,533 B2 | 12/2010 | Marczyk et al. |
| 8,034,396 B2 | 10/2011 | Kapiamba et al. |
| 8,210,411 B2 | 7/2012 | Yates et al. |
| 8,408,439 B2 | 4/2013 | Huang et al. |
| 8,453,914 B2 | 6/2013 | Laurent et al. |
| 9,186,142 B2 | 11/2015 | Fanelli et al. |
| 9,271,706 B2 | 3/2016 | Stopek et al. |
| 9,364,233 B2 | 6/2016 | Alexander, III et al. |
| 9,517,065 B2 | 12/2016 | Simms et al. |
| 9,622,746 B2 | 4/2017 | Simms et al. |
| 9,649,110 B2 | 5/2017 | Parihar et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,421 B2 | 12/2017 | Zerkle et al. |
| 9,907,554 B2 | 3/2018 | Morgan et al. |
| 10,092,292 B2 | 10/2018 | Boudreaux et al. |
| 10,166,023 B2 | 1/2019 | Vendely et al. |
| 10,349,939 B2 | 7/2019 | Shelton, IV et al. |
| 10,426,481 B2 | 10/2019 | Aronhalt et al. |
| 10,441,285 B2 | 10/2019 | Shelton, IV et al. |
| 10,524,788 B2 | 1/2020 | Vendely et al. |
| 10,568,621 B2 | 2/2020 | Shelton, IV et al. |
| 10,588,623 B2 | 3/2020 | Schmid et al. |
| 10,624,861 B2 | 4/2020 | Widenhouse et al. |
| 10,639,039 B2 | 5/2020 | Vendely et al. |
| 10,667,808 B2 | 6/2020 | Baxter, III et al. |
| 10,758,398 B2 | 9/2020 | Murthy Aravalli et al. |
| 10,945,731 B2 | 3/2021 | Baxter, III et al. |
| 10,966,722 B2 | 4/2021 | Shelton, IV et al. |
| 10,987,107 B2 | 4/2021 | Sgroi, Jr. et al. |
| 11,058,425 B2 | 7/2021 | Widenhouse et al. |
| 11,382,625 B2 | 7/2022 | Huitema et al. |
| 11,660,093 B2 | 5/2023 | Bakos et al. |
| 11,857,190 B2 | 1/2024 | Strang et al. |
| 2002/0165563 A1 | 11/2002 | Grant et al. |
| 2005/0263562 A1 | 12/2005 | Shelton, IV et al. |
| 2009/0020584 A1 | 1/2009 | Soltz et al. |
| 2009/0206143 A1 | 8/2009 | Huitema et al. |
| 2010/0331880 A1 | 12/2010 | Stopek et al. |
| 2011/0077629 A1* | 3/2011 | Tanaka .................. A61B 18/085 606/41 |
| 2012/0080336 A1 | 4/2012 | Shelton, IV et al. |
| 2012/0080498 A1 | 4/2012 | Shelton, IV et al. |
| 2012/0080503 A1 | 4/2012 | Woodard, Jr. et al. |
| 2012/0083836 A1 | 4/2012 | Shelton, IV et al. |
| 2012/0125792 A1* | 5/2012 | Cassivi ............ A61B 17/07292 227/175.1 |
| 2012/0136345 A1* | 5/2012 | Takashino .......... A61B 18/1445 606/41 |
| 2012/0241492 A1 | 9/2012 | Shelton, IV et al. |
| 2012/0241503 A1 | 9/2012 | Baxter, III et al. |
| 2012/0241505 A1* | 9/2012 | Alexander, III ... A61B 17/1155 227/179.1 |
| 2013/0146641 A1 | 6/2013 | Shelton, IV et al. |
| 2013/0146643 A1 | 6/2013 | Schmid et al. |
| 2013/0153635 A1* | 6/2013 | Hodgkinson .... A61B 17/07207 227/176.1 |
| 2013/0214030 A1 | 8/2013 | Aronhalt et al. |
| 2013/0221062 A1 | 8/2013 | Hodgkinson |
| 2013/0256376 A1 | 10/2013 | Barton et al. |
| 2014/0131419 A1* | 5/2014 | Bettuchi .......... A61B 17/07292 227/176.1 |
| 2014/0158741 A1* | 6/2014 | Woodard, Jr. ....... A61B 17/072 227/175.1 |
| 2014/0166721 A1* | 6/2014 | Stevenson ............ A61B 17/072 227/176.1 |
| 2014/0209658 A1 | 7/2014 | Skalla et al. |
| 2014/0224686 A1* | 8/2014 | Aronhalt ............ A61B 17/0644 206/339 |
| 2014/0291382 A1 | 10/2014 | Lloyd et al. |
| 2015/0136831 A1 | 5/2015 | Baxter, III et al. |
| 2015/0196296 A1 | 7/2015 | Swayze et al. |
| 2015/0196348 A1* | 7/2015 | Yates ............... A61B 17/07207 227/182.1 |
| 2015/0282809 A1* | 10/2015 | Shelton, IV ......... A61B 17/068 227/176.1 |
| 2016/0278764 A1 | 9/2016 | Shelton, IV et al. |
| 2016/0278765 A1* | 9/2016 | Shelton, IV ..... A61B 17/07207 |
| 2016/0278774 A1* | 9/2016 | Shelton, IV ..... A61B 17/07292 |
| 2017/0055981 A1* | 3/2017 | Vendely .......... A61B 17/07292 |
| 2017/0055986 A1 | 3/2017 | Harris et al. |
| 2017/0086838 A1* | 3/2017 | Harris .................. A61B 17/105 |
| 2017/0086841 A1* | 3/2017 | Vendely ................... B05D 1/30 |
| 2017/0086845 A1* | 3/2017 | Vendely ............. A61B 17/0644 |
| 2017/0119390 A1 | 5/2017 | Schellin et al. |
| 2017/0119392 A1 | 5/2017 | Shelton, IV et al. |
| 2018/0103952 A1 | 4/2018 | Aronhalt et al. |
| 2018/0235624 A1* | 8/2018 | Shelton, IV ..... A61B 17/07292 |
| 2018/0235626 A1* | 8/2018 | Shelton, IV ..... A61B 17/07207 |
| 2019/0008518 A1 | 1/2019 | Sgroi, Jr. et al. |
| 2019/0200978 A1 | 7/2019 | Shelton, IV et al. |
| 2019/0269402 A1 | 9/2019 | Murray et al. |
| 2019/0298338 A1 | 10/2019 | Vendely et al. |
| 2019/0314016 A1 | 10/2019 | Huitema et al. |
| 2019/0314018 A1 | 10/2019 | Huitema et al. |
| 2020/0205825 A1 | 7/2020 | Vendely et al. |
| 2020/0305963 A1* | 10/2020 | Wagner ............. A61B 18/1445 |
| 2020/0390944 A1* | 12/2020 | Williams ............... A61B 17/80 |
| 2021/0128129 A1* | 5/2021 | George ................. A61L 31/041 |
| 2022/0061843 A1 | 3/2022 | Vendely et al. |
| 2022/0160360 A1* | 5/2022 | Harris ............. A61B 17/07292 |
| 2022/0313247 A1 | 10/2022 | Shelton, IV et al. |
| 2023/0301656 A1 | 9/2023 | Seow et al. |
| 2023/0301674 A1 | 9/2023 | Rector et al. |
| 2023/0301675 A1 | 9/2023 | Seow et al. |
| 2023/0320742 A1 | 10/2023 | Bakos et al. |

FOREIGN PATENT DOCUMENTS

| | | |
|---|---|---|
| EP | 3150142 A2 | 4/2017 |
| EP | 3162384 A1 | 5/2017 |
| EP | 3363387 A1 | 8/2018 |
| EP | 3424441 A2 | 1/2019 |
| EP | 3530213 A2 | 8/2019 |
| EP | 3791802 A1 | 3/2021 |
| EP | 3791805 A1 | 3/2021 |
| EP | 3791806 A1 | 3/2021 |

OTHER PUBLICATIONS

International Search Report and Written Opinion dated Jul. 31, 2023, for International Application No. PCT/IB2023/052804, 21 pages.

International Search Report and Written Opinion dated Aug. 7, 2023, for International Application No. PCT/IB2023/052805, 21 pages.

International Search Report and Written Opinion dated Aug. 9, 2023, for International Application No. PCT/IB2023/052809, 20 pages.

International Search Report and Written Opinion dated Jun. 20, 2023, for International Application No. PCT/IB2023/052810, 16 pages.

* cited by examiner

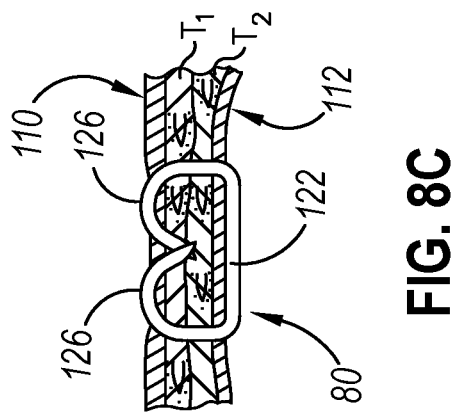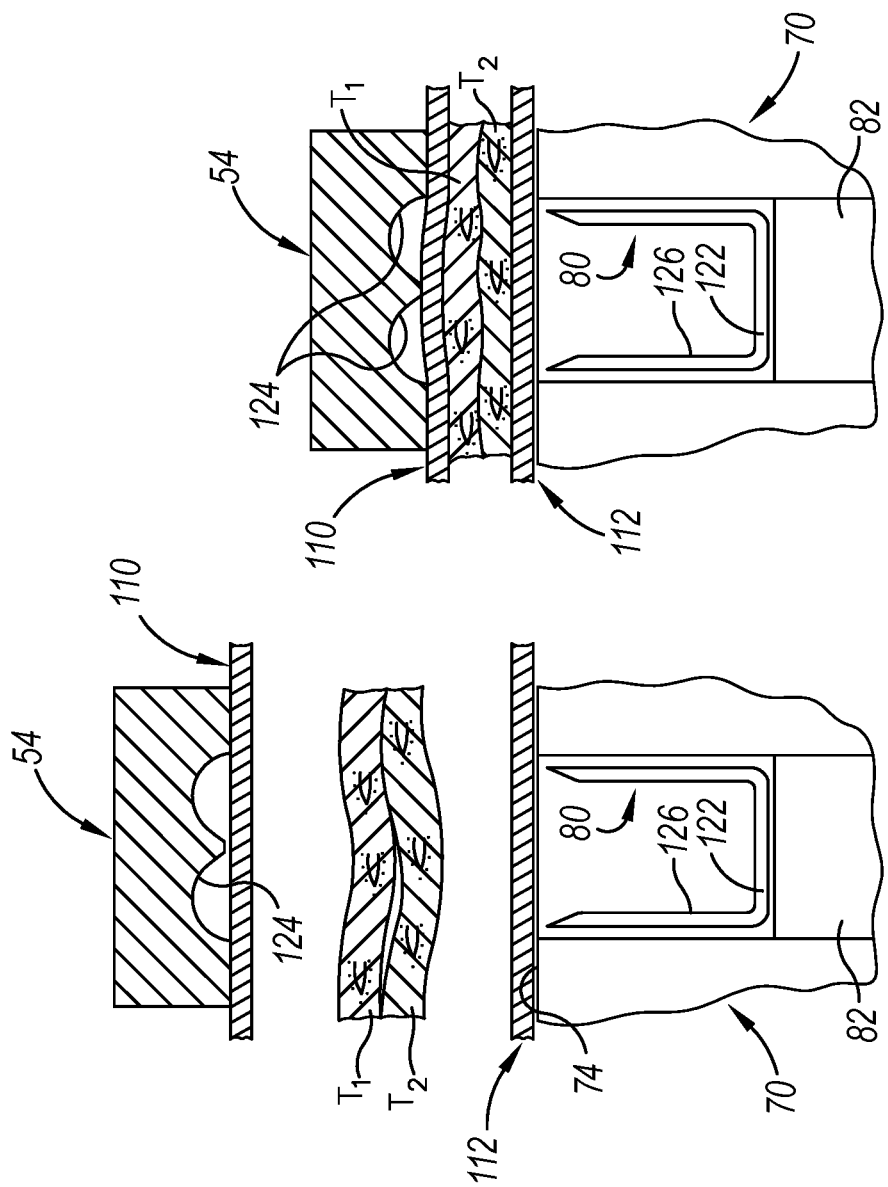

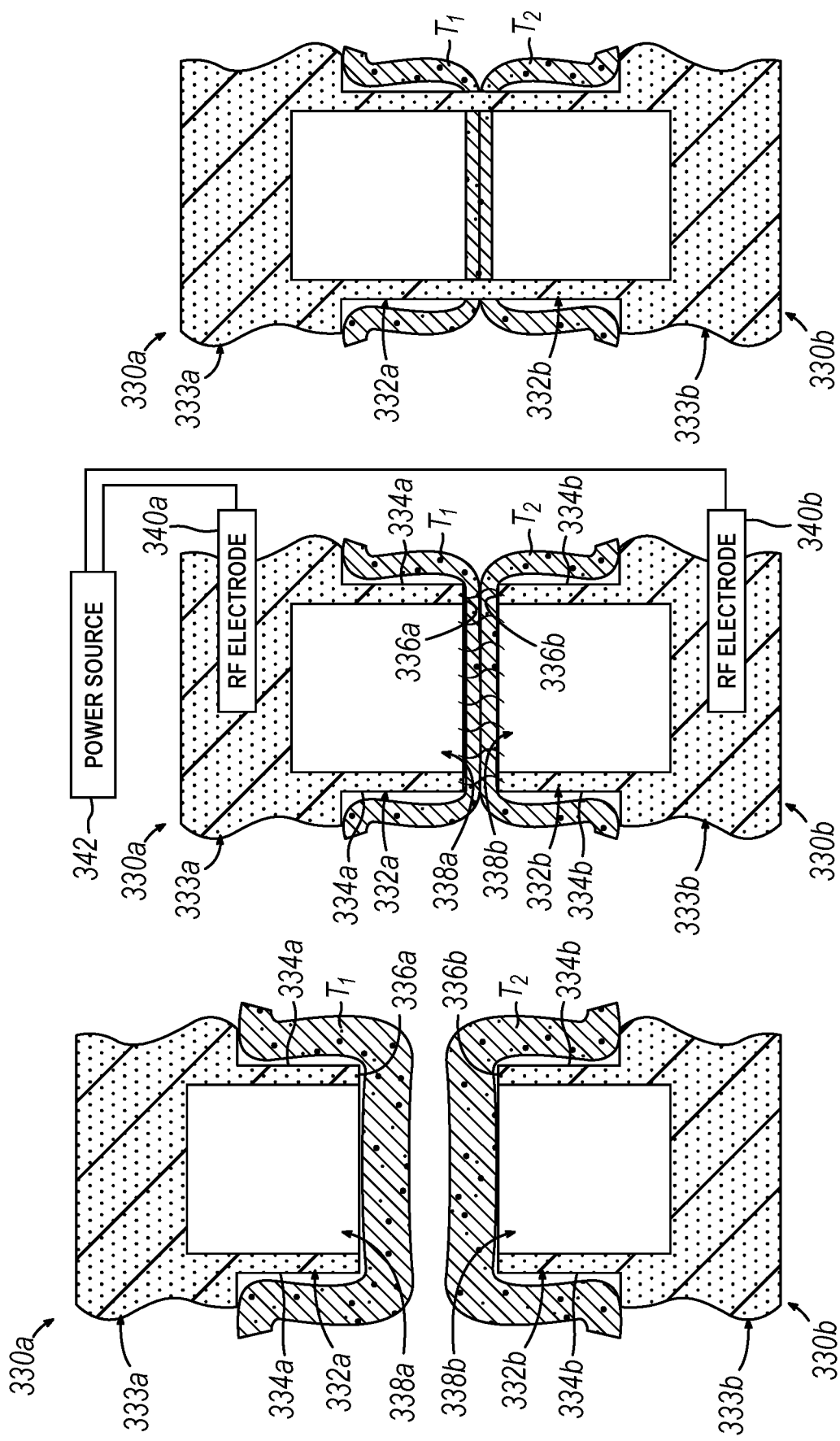

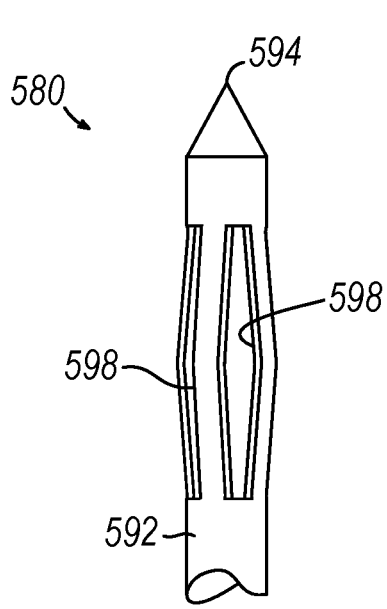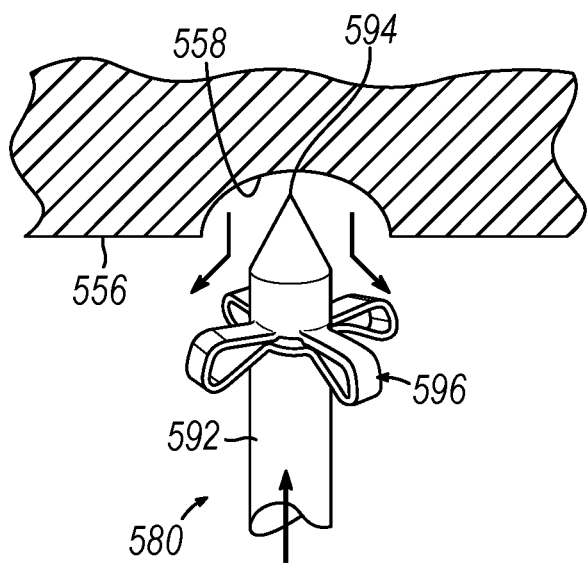
FIG. 15A  FIG. 15B
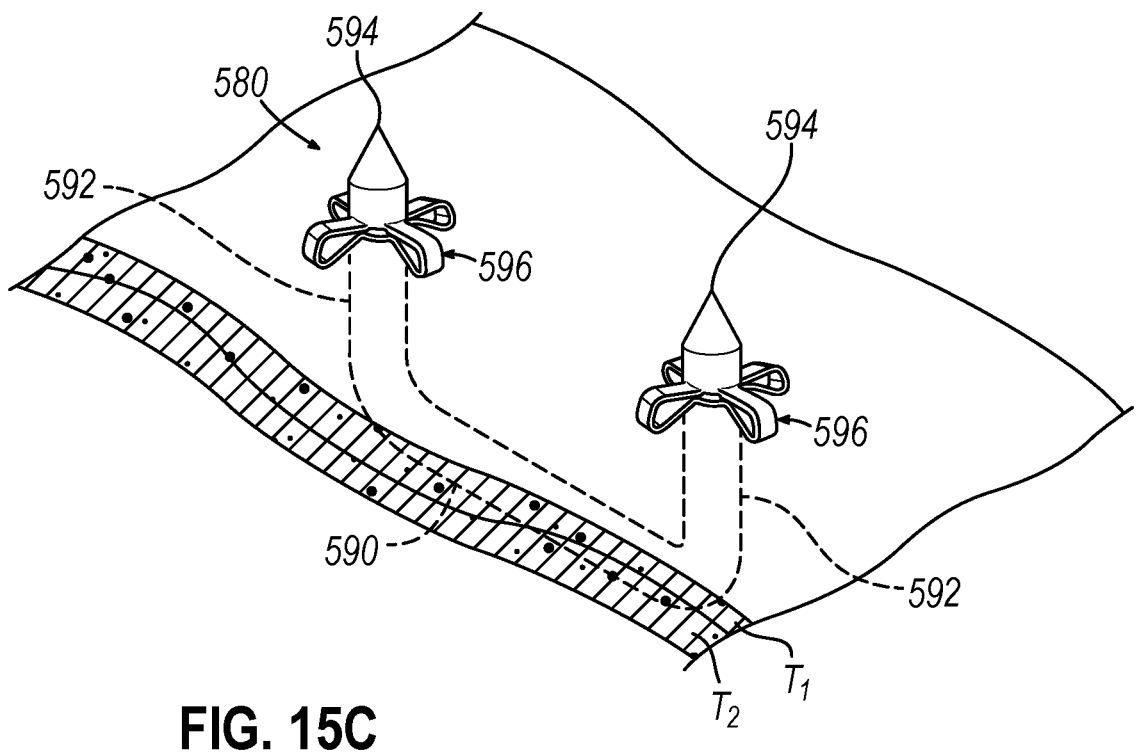
FIG. 15C

THERMALLY FORMED TISSUE CUSHION ADJUNCT FOR SURGICAL STAPLER END EFFECTOR

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 8A depicts a cross-sectional end view of a portion of the end effector of FIG. 3 with the buttress assemblies of FIG. 7 applied to the upper and lower jaws of the end effector, showing the end effector jaws in an open state with tissue positioned between the upper and lower jaws;

FIG. 8B depicts a cross-sectional end view of the end effector and buttress assemblies of FIG. 8A, showing the end effector jaws in a closed state on the tissue;

FIG. 8C depicts a cross-sectional view of a formed staple and the buttress assemblies of FIG. 8A after having been secured to the tissue by the end effector of FIG. 3;

FIG. 13A depicts a cross-sectional view of a pair of exemplary thermally-bondable adjuncts with tissue layers positioned therebetween;

FIG. 13B depicts a cross-sectional view of the adjuncts of FIG. 13A compressing the tissue layers therebetween, showing heating of confronting surfaces of the adjuncts;

FIG. 13C depicts a cross-sectional view of the adjuncts of FIG. 13A thermally bonded to each other to secure the adjuncts to the tissue layers;

FIG. 15A depicts a partial side elevational view of an exemplary fastener having at least one mechanically-expandable leg, showing the at least one leg in an undeformed state;

FIG. 15B depicts a partial perspective view of the fastener of FIG. 15A, schematically showing the at least one leg being driven against a corresponding pocket of the anvil of FIG. 3 to be deformed thereby;

FIG. 15C depicts a perspective view of the fastener of FIG. 15A, showing the legs of the fastener mechanically expanded to define respective anchors for capturing at least one tissue layer;

Figure 1:
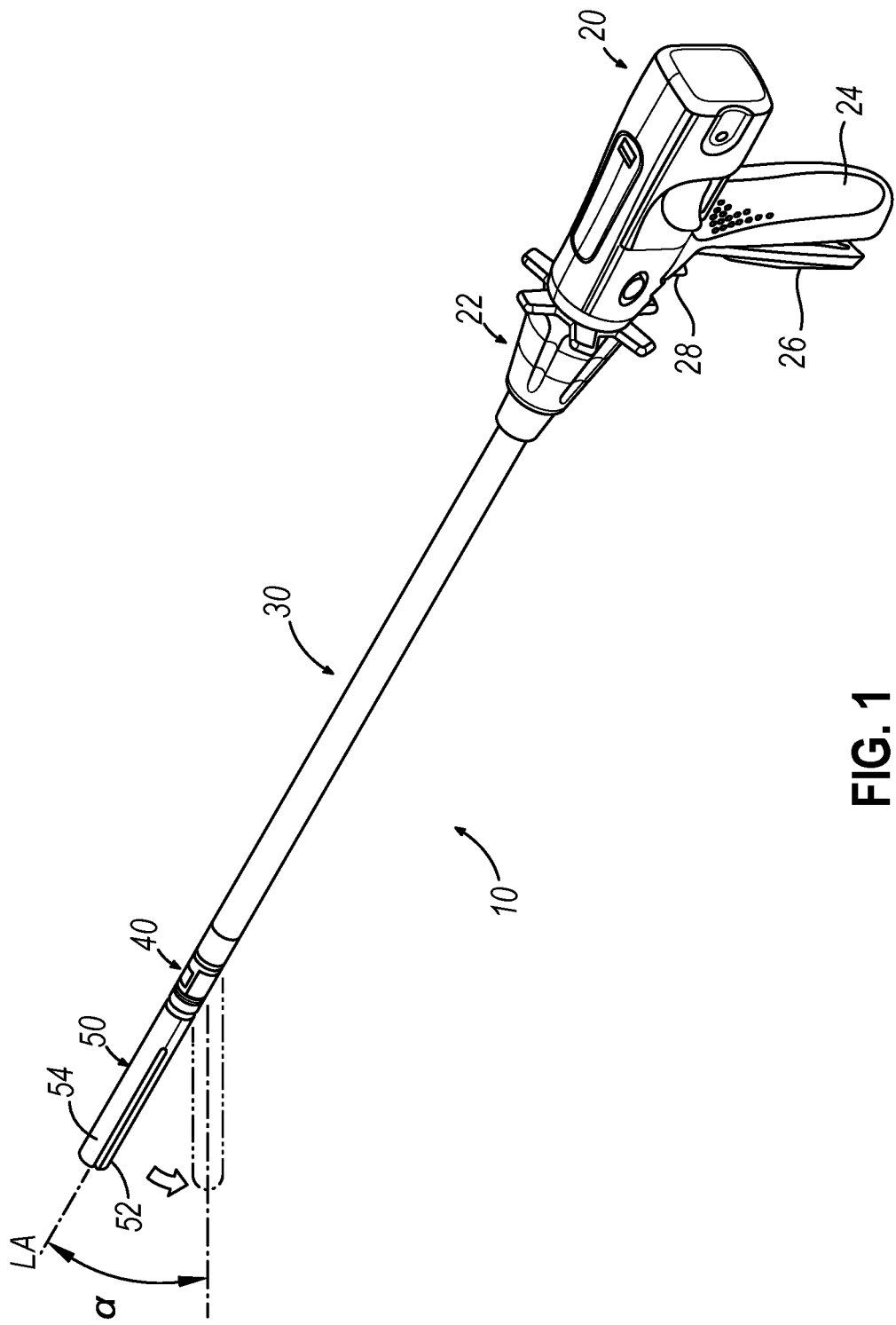
FIG. 1 depicts a perspective view of an exemplary surgical stapler.

The drawings are not intended to be limiting in any way, and it is contemplated that various embodiments of the invention may be carried out in a variety of ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Exemplary Surgical Stapler

Figure 2:
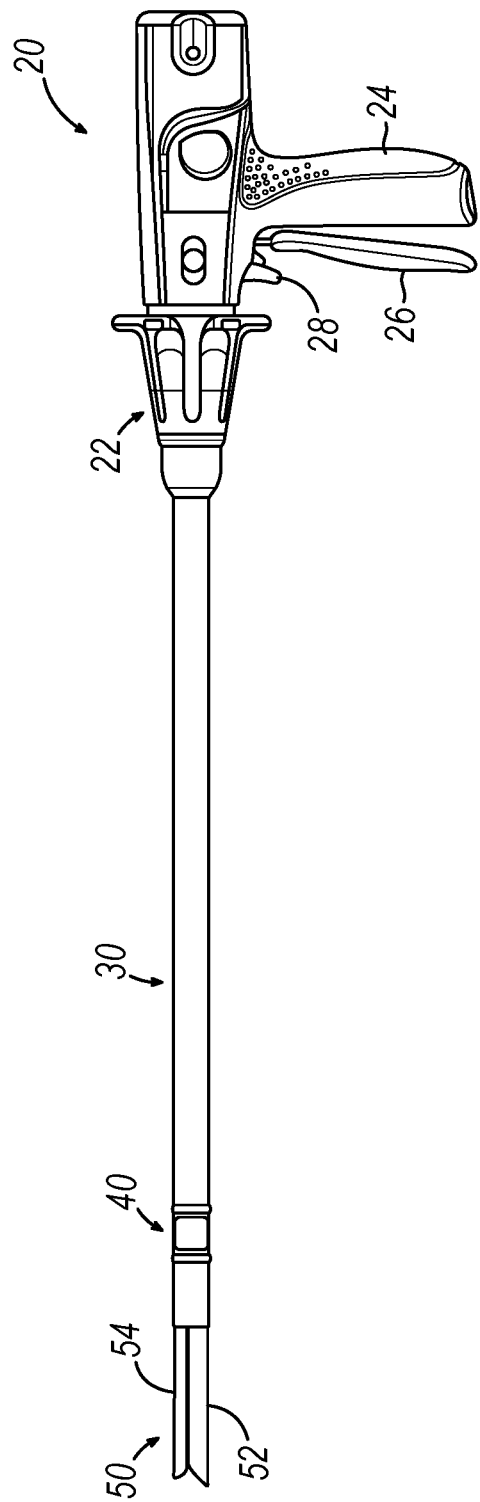
FIG. 2 depicts a side elevational view of the surgical stapler of FIG. 1.

FIGS. 1-6 show an exemplary surgical stapler (10) that is sized for insertion through a trocar cannula or an incision (e.g., thoracotomy, etc.) to a surgical site in a patient for performing a surgical procedure. As shown in FIGS. 1 and 2, surgical stapler (10) of the present example includes a proximal body in the form of a handle assembly (20), a shaft assembly (30) extending distally from handle assembly (20) and terminating at an articulation joint (40), and an end effector (50) coupled with the distal end of shaft assembly (30) via articulation joint (40). Articulation joint (40) is configured to enable lateral deflection, either actively or passively, of end effector (50) relative to a longitudinal axis (LA) of shaft assembly (30) to a desired angle (α) via actuation of an articulation control feature (22) of handle assembly (20).

Figure 3:
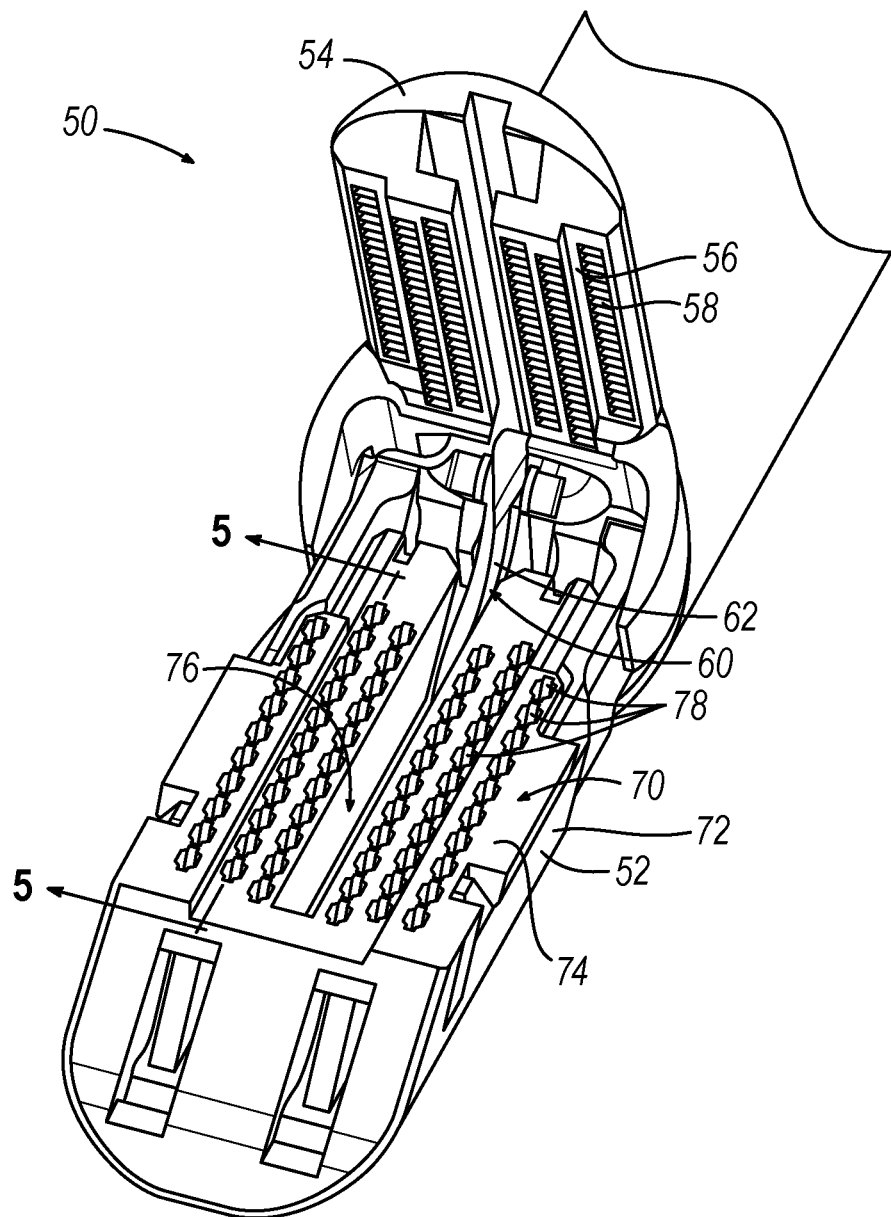
FIG. 3 depicts a perspective view of an end effector of the surgical stapler of FIG. 1 in an open state.
Figure 4:
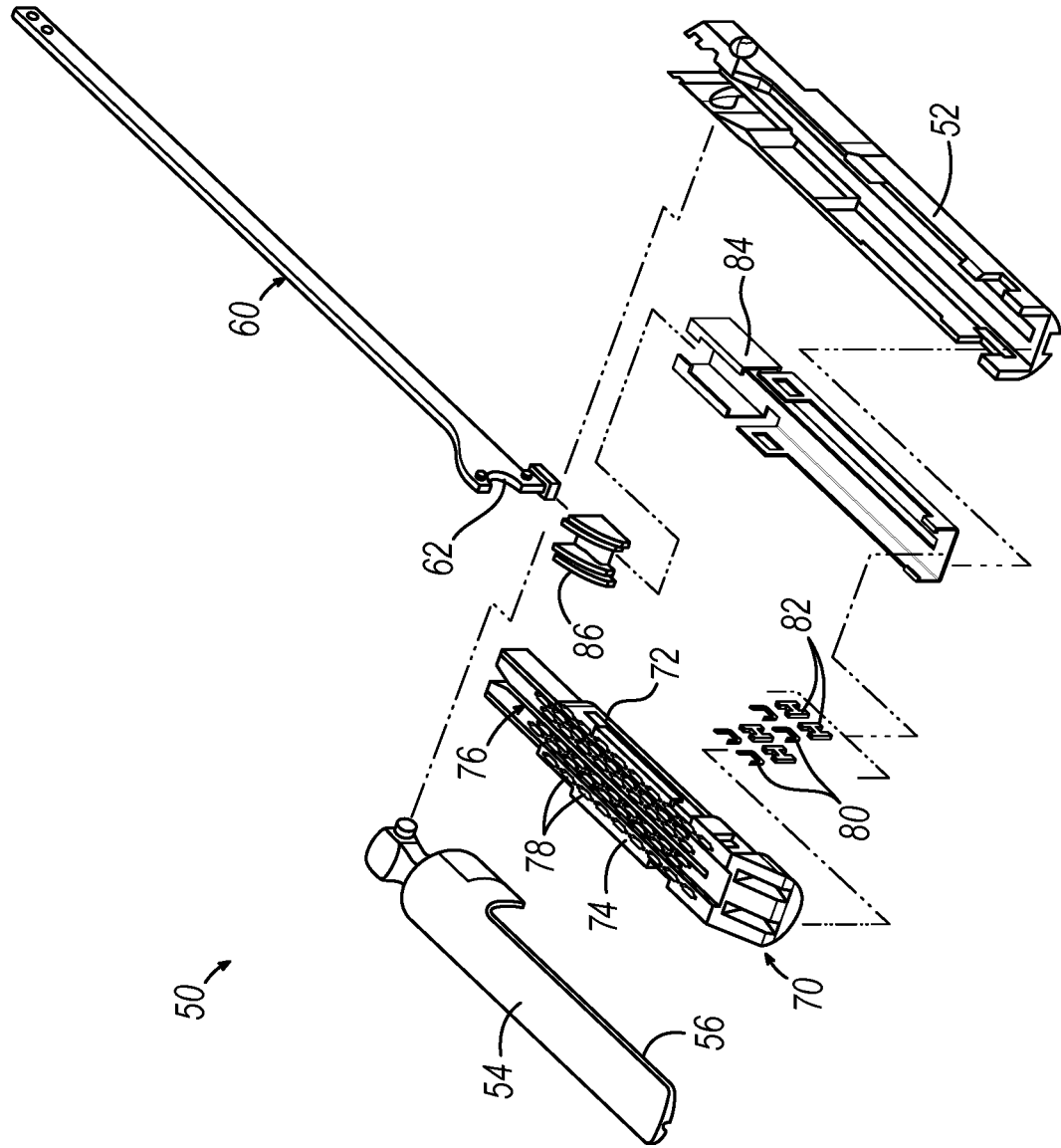
FIG. 4 depicts an exploded perspective view of the end effector of FIG. 3.

As shown best in FIGS. 3 and 4, end effector (50) includes a lower jaw (52) that supports a stapling assembly in the form of a replaceable staple cartridge (70), and an upper jaw (54) that presents an anvil (56) having a plurality of staple forming pockets (58). Upper jaw (54) is configured to pivot relative to lower jaw (52) to clamp tissue between staple cartridge (70) and anvil (56) and subsequently form staples deployed by staple cartridge (70). End effector (50) further includes an elongate firing member (60) configured to translate distally through end effector (50) to drive staples from staple cartridge (70) toward anvil (56) and simultaneously cut tissue with a distally presented cutting edge (62). Accordingly, end effector (50) is operable to clamp, staple, and cut tissue.

As shown best in FIGS. 1 and 2, handle assembly (20) further includes a pistol grip (24), a closure trigger (26), and a firing trigger (28). Closure trigger (26) is pivotable toward pistol grip (24) to pivotably actuate upper jaw (54) toward lower jaw (52) and thereby close end effector (50) on tissue. Firing trigger (28) is then pivotable toward pistol grip (24) to fire end effector (50) on the clamped tissue. More specifically, actuation of firing trigger (28) causes firing member (60) to translate distally through end effector (50), including staple cartridge (70), to thereby staple and simultaneously cut the clamped tissue.

As shown in FIGS. 3-5B, staple cartridge (70) includes a cartridge body (72) having an upwardly facing deck (74), an elongate slot (76) extending along a central axis of cartridge body (72) and opening upwardly through deck (74), and a plurality of staple openings (78) (also known as apertures) extending through deck (74) on each side of elongate slot (76). Each staple opening (78) slidably houses an unformed staple (80) and a respective staple driver (82) positioned beneath staple (80). A lower tray (84), also known as a pan, encloses an underside of cartridge body (72) and thereby retains staples (80) and staple drivers (82) within cartridge body (72). A wedge sled (86) is slidably disposed within cartridge body (72) and includes upwardly presented cam surfaces configured to engage the undersides of staple drivers (82).

Figure 5A:
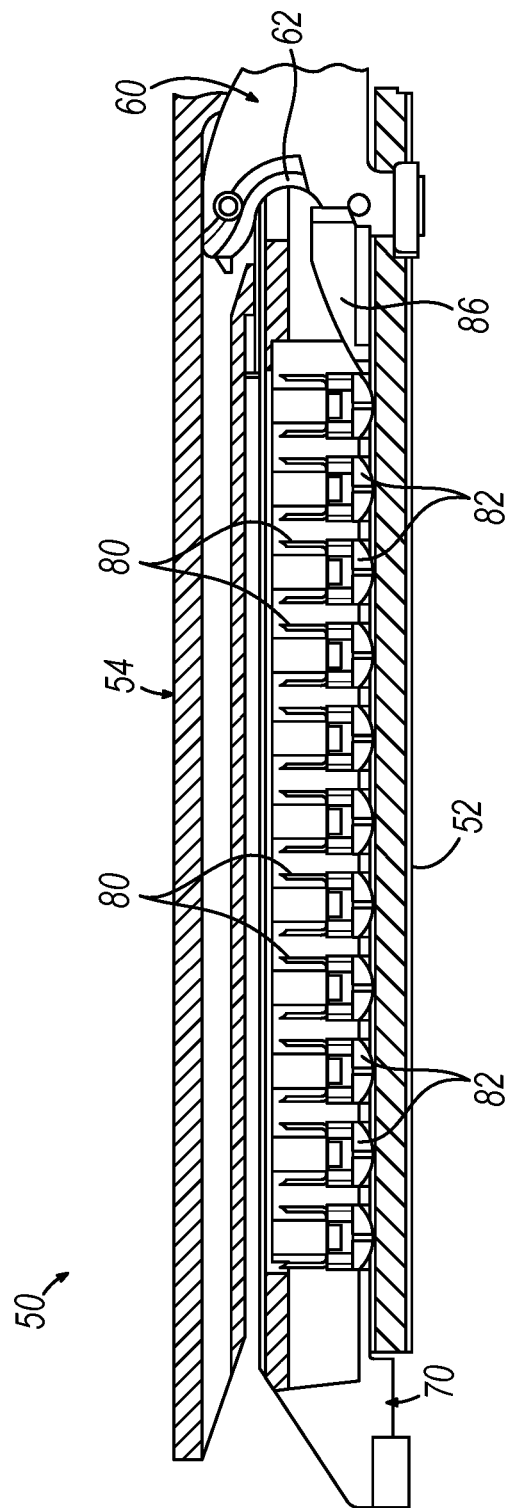
FIG. 5A depicts a side cross-sectional view of the end effector of FIG. 3, taken along line 5-5 of FIG. 3, with a firing member in a proximal position.
Figure 5B:
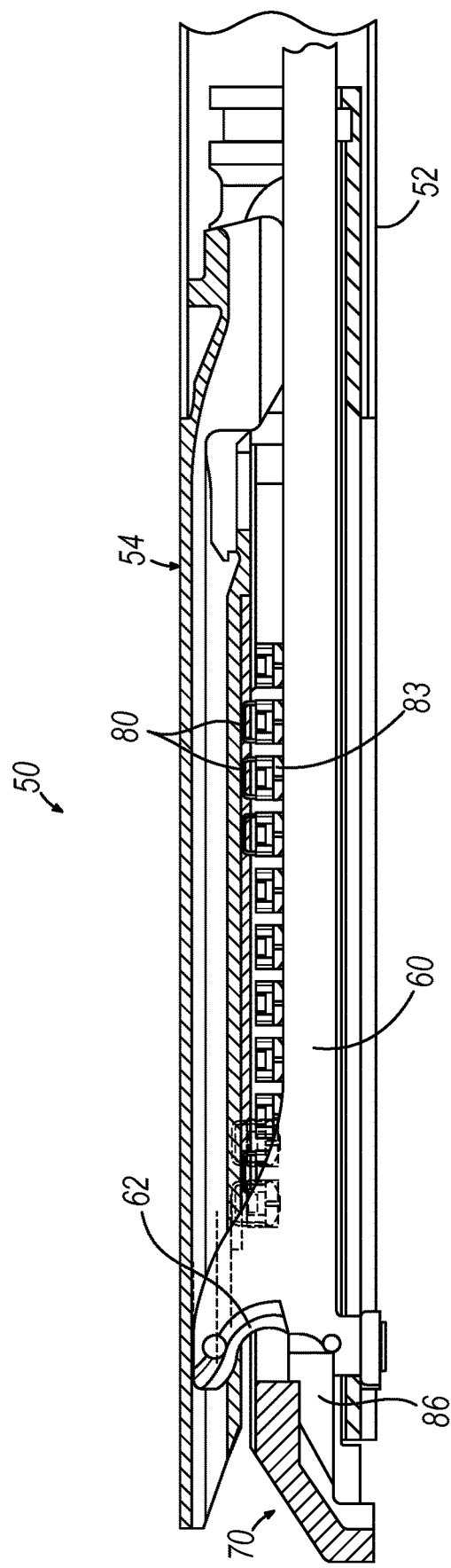
FIG. 5B depicts a side cross-sectional view of the end effector of FIG. 3, taken along line 5-5 of FIG. 3, with the firing member in a distal position.

FIGS. 5A-5B show a firing stroke of surgical stapler (10) during which firing member (60) is actuated distally through end effector (50), including elongate slot (76) of staple cartridge (70). A distal end of firing member (60) drives wedge sled (86) distally to cam staple drivers (82) upwardly and thereby drive the respective staples (80) outwardly from staple openings (78). The legs of staples (80) pass through clamped tissue (not shown) and are then formed by staple forming pockets (58) of anvil (56) (see FIG. 3). Simultaneously, the clamped tissue is severed by cutting edge (62) of firing member (60).

Figure 6:
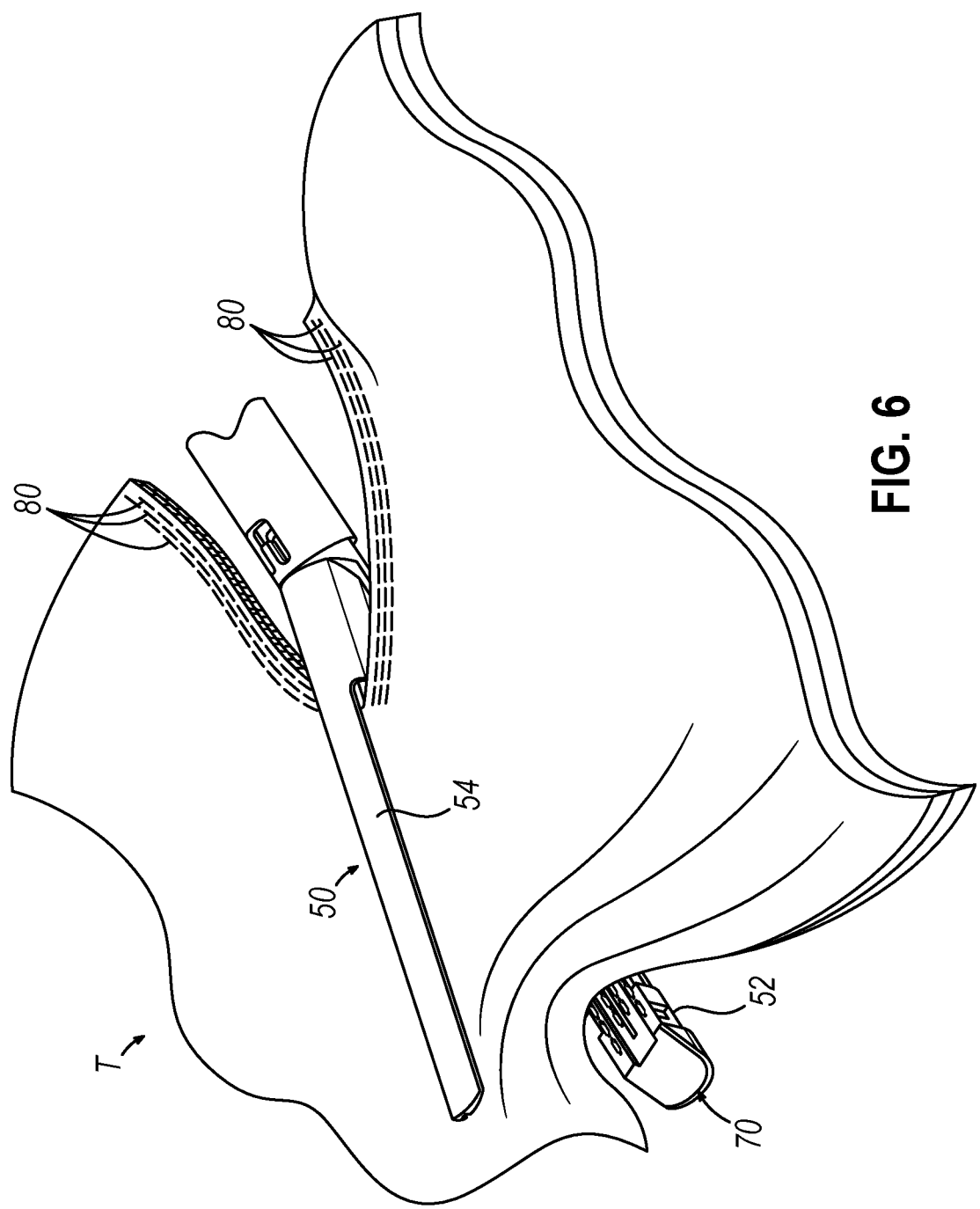
FIG. 6 depicts a perspective view of the end effector of FIG. 3, positioned at tissue and having been fired once in the tissue.

FIG. 6 shows end effector (50) after having been actuated through a single firing stroke through tissue (T). Cutting edge (62) of firing member (60) has cut through tissue (T), and staple drivers (82) have driven three alternating rows of staples (80) through tissue (T) on each side of the cut line produced by cutting edge (62). After the first firing stroke is completed, end effector (50) is withdrawn from the patient, spent staple cartridge (70) is replaced with a new staple cartridge (70), and end effector (50) is then again inserted into the patient to reach the stapling site for further cutting and stapling. This process may be repeated until the desired quantity and pattern of firing strokes across the tissue (T) has been completed.

Surgical stapler (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly

In some instances, it may be desirable to equip end effector (50) of surgical stapler (10) with an adjunct, also known as a buttress or a tissue thickness compensator, to reinforce the mechanical fastening of tissue provided by staples (80). Such a buttress may prevent the applied staples (80) from pulling through the tissue and may otherwise reduce a risk of tissue tearing at or near the site of applied staples (80). In addition to or as an alternative to providing structural support and integrity to a line of staples (80), a buttress may provide various other kinds of effects such as spacing or gap-filling, administration of therapeutic agents, and/or other effects. In some instances, a buttress may be provided on upper deck (74) of staple cartridge (70). In some other instances, a buttress may be provided on the surface of anvil (56) that faces staple cartridge (70). It should also be understood that a first buttress may be provided on upper deck (74) of staple cartridge (70) while a second buttress is provided on anvil (56) of the same end effector (50).

A. Exemplary Composition of Buttress Assembly

Figure 7:
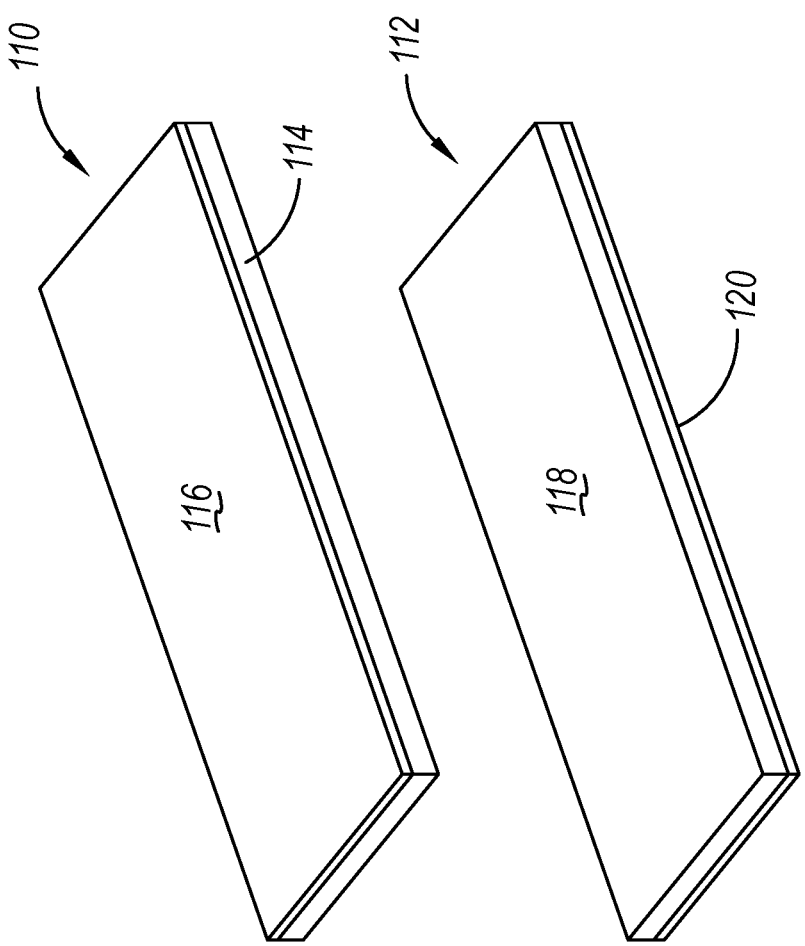
FIG. 7 depicts a perspective view of an exemplary pair of adjuncts in the form of buttress assemblies, each of which may be applied to a jaw of the end effector of FIG. 3.

FIG. 7 shows an exemplary pair of adjuncts in the form of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (80). By way of example only, each buttress body (114, 118) may comprise a mesh of polyglactin 910 material by Ethicon, Inc. of Somerville, New Jersey. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to an underside (124) of anvil (56). Similarly, adhesive layer (120) is provided on buttress body (118) to adhere buttress body (118) to upper deck (74) of staple cartridge (70). Such an adhesive material may provide proper positioning of buttress body (114, 118) before and during actuation of end effector (50); then allow buttress body (114, 118) to separate from end effector (50) after end effector (50) has been actuated, without causing damage to buttress body (114, 118) that is substantial enough to compromise the proper subsequent functioning of buttress body (114, 118).

B. Exemplary Stapling of Tissue with Buttress Assemblies

FIGS. 8A-8C show an exemplary sequence in which surgical stapler end effector (50), which has been loaded with buttress assemblies (110, 112), is actuated to drive staples (80) through two opposed layers of tissue ($T_1$, $T_2$), with buttress assemblies (110, 112) being secured to the same layers of tissue ($T_1$, $T_2$) by staples (80). In particular, FIG. 8A shows layers of tissue ($T_1$, $T_2$) positioned between anvil (56) and staple cartridge (70), with anvil (56) in the open position. Buttress assembly (110) is adhered to underside (124) of anvil (56) via adhesive layer (116); while buttress assembly (112) is adhered to upper deck (74) of staple cartridge (70) via adhesive layer (120). Layers of tissue ($T_1$, $T_2$) are thus interposed between buttress assemblies (110, 112). Next, anvil (56) is closed against staple cartridge (70) such that layers of tissue ($T_1$, $T_2$) are compressed between anvil (56) and staple cartridge (70), with buttress assemblies (110, 112) engaging opposite surfaces of tissue layers ($T_1$, $T_2$). End effector (50) is then fired as described above, driving staple (80) through buttress assemblies (110, 112) and tissue ($T_1$, $T_2$). As shown in FIG. 8C, a crown (122) of driven staple (80) captures and retains buttress assembly (112) against layer of tissue ($T_2$). Deformed legs (126) of staple (80) capture and retain buttress assembly (110) against layer of tissue ($T_1$).

Figure 9:
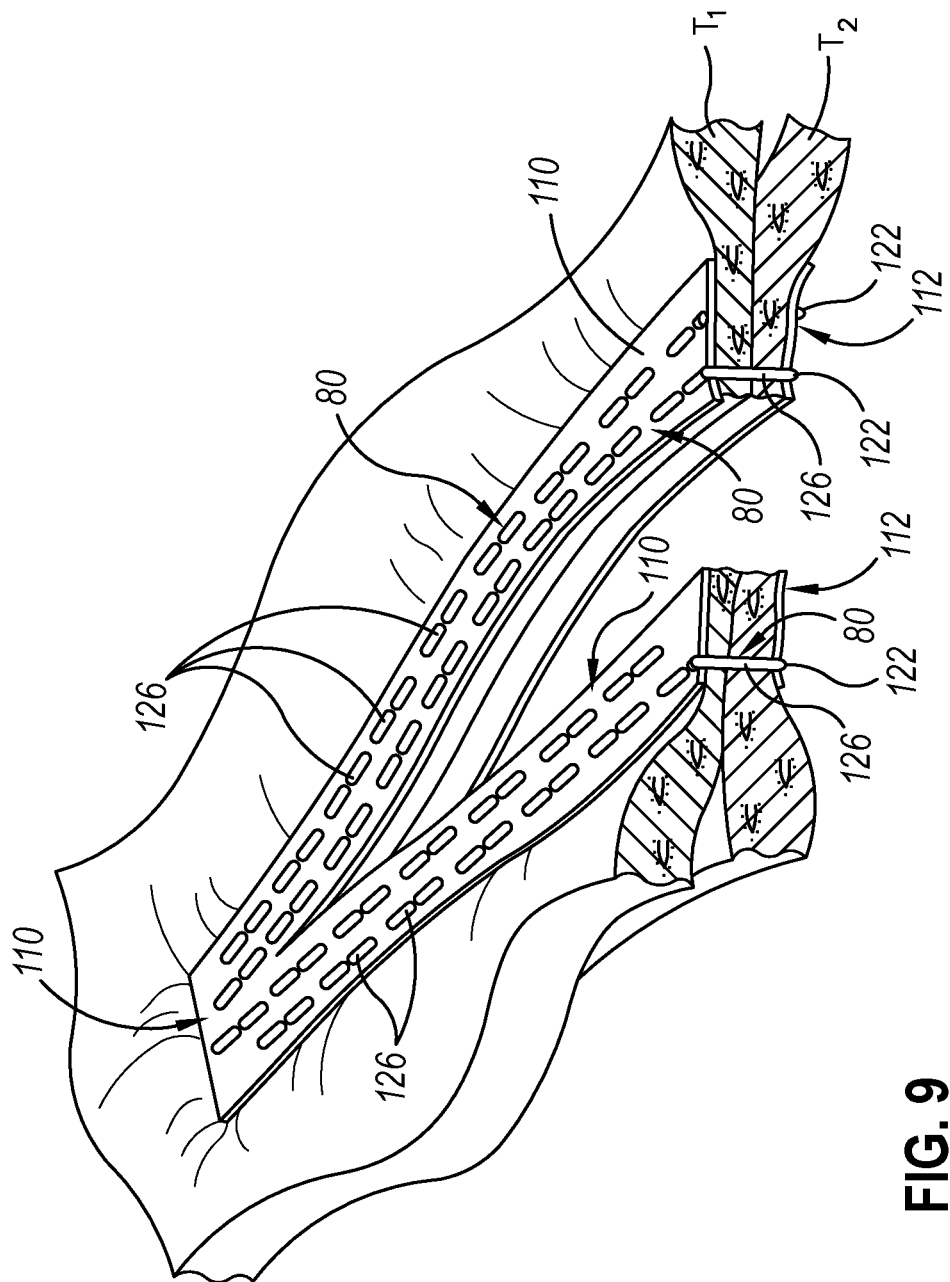
FIG. 9 depicts a perspective view of formed staples and the buttress assemblies of FIG. 8A after having been secured to the tissue by the end effector of FIG. 3.
Figure 10:
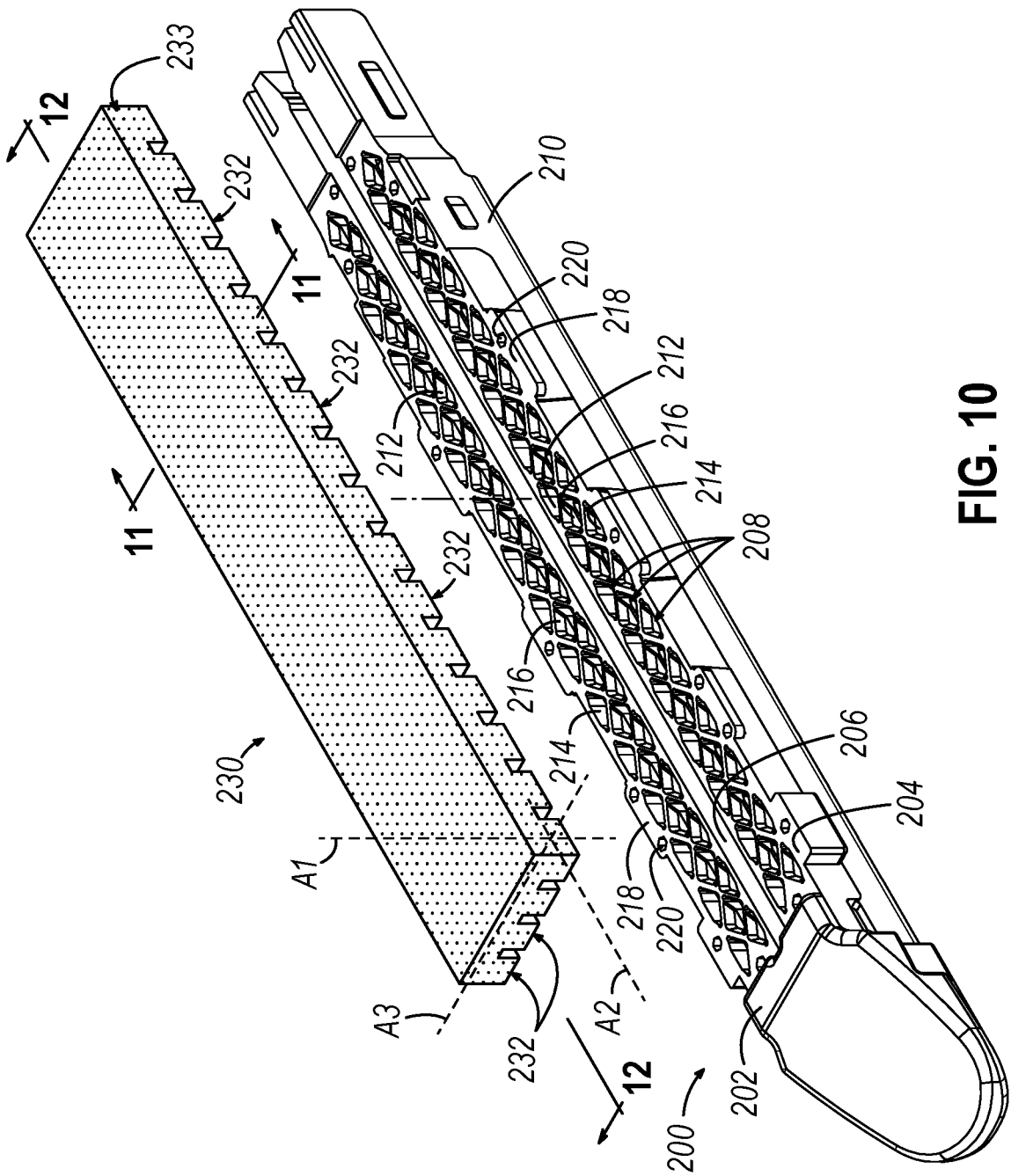
FIG. 10 depicts a perspective view of another exemplary staple cartridge in combination with a first alternative exemplary adjunct.

A series of staples (80) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (50) is pulled away from tissue ($T_1$, $T_2$) after deploying staples (80) and buttress assemblies (110, 112), buttress assemblies (110, 112) disengage end effector such that buttress assemblies (110, 112) remain secured to tissue ($T_1$, $T_2$) with staples (80). Buttress assemblies (110, 112) thus provide structural reinforcement to the lines of staples (80) formed in tissue ($T_1$, $T_2$). As can also be seen in FIG. 9, distally presented cutting edge (62) of firing member (60) also cuts through a centerline of buttress assemblies (110, 112), separating each buttress assembly (110, 112) into a corresponding pair of sections, such that each section remains secured to a respective severed region of tissue ($T_1$, $T_2$).

During use, surgical instrument (10) may be actuated multiple times during a single surgical procedure such that it may be desirable to enable an operator to repeatedly and easily load buttress assemblies (110, 112) onto lower jaw and anvil (16, 18) during that single surgical procedure. Accordingly, it may be desirable to use an adjunct applicator, also referred to as a buttress applier cartridge, to apply buttress assemblies (110, 112) to lower jaw and anvil (16, 18). Exemplary versions of such an applicator are disclosed in U.S. patent application Ser. No. 17/022,520, entitled "Method of Applying Buttress to End Effector of Surgical Stapler," filed Sep. 16, 2020, issued as U.S. Pat. No. 11,660,093 on May 30, 2023, the disclosure of which is incorporated by reference herein.

It will be appreciated that exemplary adjuncts and adjunct applicators may be further configured in accordance with one or more teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and U.S. Pat. Pub. No. 2012/0080336, entitled "Staple Cartridge Comprising Staples Positioned Within a Compressible Portion Thereof," published Apr. 5, 2012, now abandoned, the disclosures of which are incorporated by reference herein.

III. Exemplary Compressible Adjunct

Figure 11:
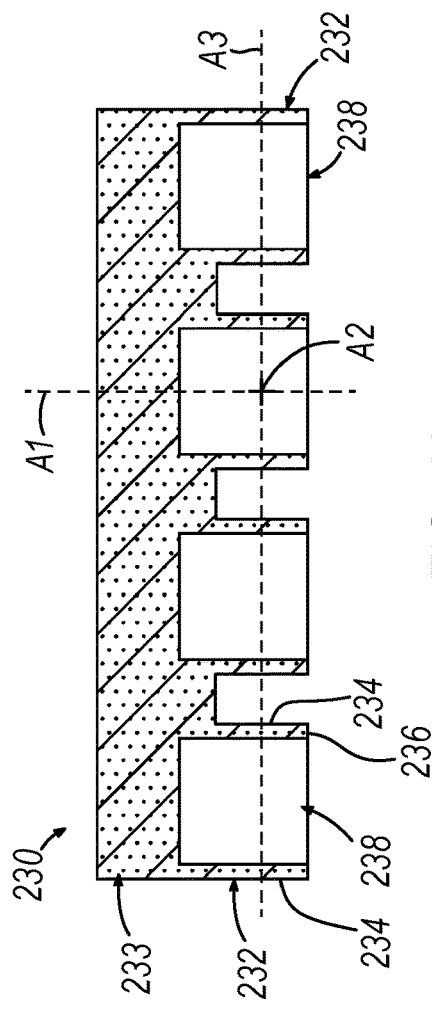
FIG. 11 depicts a cross-sectional view of the adjunct of FIG. 10, taken along line 11-11 of FIG. 10.
Figure 12:
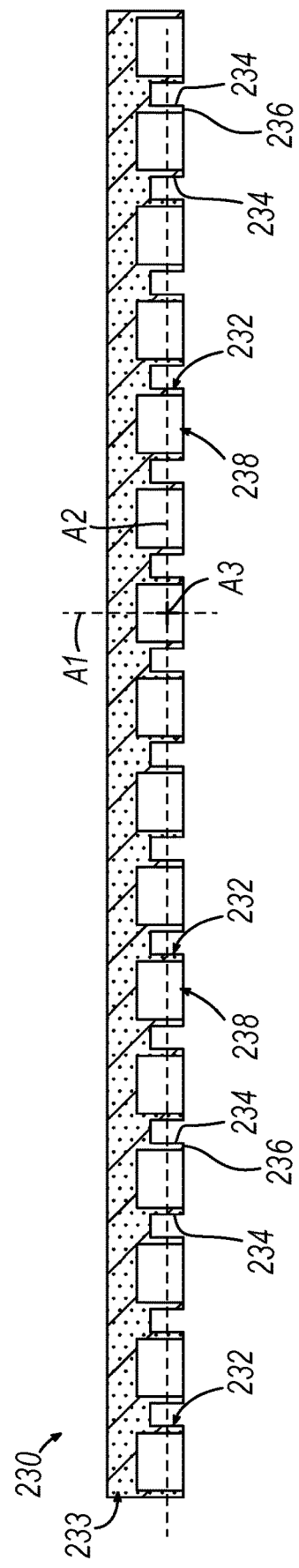
FIG. 12 depicts a cross-sectional view of the adjunct of FIG. 10, taken along line 12-12 of FIG. 10.

In some instances, it may be desirable to employ an adjunct having an enhanced degree of compressibility in a direction orthogonal to the stapling surfaces of end effector (50). Such an adjunct may be configured to apply a compression spring force to stapled tissue consistently along the entire length of the formed staple pattern, thereby ensuring a secure seal of tissue having a thickness that varies along a length of the formed staple pattern and end effector (50). FIGS. 10-12 show an example of such an adjunct (230), also referred to herein as a buttress or cushion, in combination with a staple cartridge (200). Staple cartridge (200) and adjunct (230) are configured for use with end effector (50) and are similar to staple cartridge (70) and buttress assembly (110, 112) described above except as otherwise described below.

It will be appreciated that staple cartridge (200) and/or adjunct (230) may be further configured in accordance with teachings of any one of more the following references, the disclosures of which are incorporated by reference herein: U.S. Pat. No. 10,441,285, entitled "Tissue Thickness Compensator Comprising Tissue Ingrowth Features," issued Oct. 15, 2019; U.S. Pat. No. 10,524,788, entitled "Compressible Adjunct with Attachment Regions," issued Jan. 7, 2020; U.S. Pat. No. 10,568,621, entitled "Surgical Staple Buttress with Integral Adhesive for Releasably Attaching to a Surgical Stapler," issued Feb. 25, 2020; U.S. Pat. No. 10,588,623, entitled "Adhesive Film Laminate," issued Mar. 17, 2020; U.S. Pat. No. 10,624,861, entitled "Tissue Thickness Compensator Configured to Redistribute Compressive Forces," issued Apr. 21, 2020; U.S. Pat. No. 10,667,808, entitled "Staple Cartridge Comprising an Absorbable Adjunct," issued Jun. 2, 2020; U.S. Pat. No. 10,945,731, entitled "Tissue Thickness Compensator Comprising Controlled Release and Expansion," issued Mar. 16, 2021; U.S. Pat. No. 10,966,722, entitled "Adjunct Materials and Methods of Using Same in Surgical Methods for Tissue Sealing," issued Apr. 6, 2021; U.S. Pat. No. 11,058,425, entitled "Implantable Layers for a Surgical Instrument," issued Jul. 13, 2021; and U.S. Pat. Pub. No. 2019/0200978, entitled "Tissue Ingrowth Materials and Method of Using the Same," published Jul. 4, 2019, issued as U.S. Pat. No. 11,219,451 on Jan. 11, 2022.

As shown in FIG. 10, staple cartridge (200) includes a cartridge body (202) having an upwardly facing deck (204), an elongate slot (206) extending along a central axis of cartridge body (202) and opening upwardly through deck (204), and a plurality of staple openings (208) extending through deck (204) on each side of elongate slot (206). Each staple opening (208) slidably houses an unformed staple (not shown), similar to staple (80), and a respective staple driver (not shown), similar to staple driver (82), configured to drive the staple outwardly toward anvil (56) to be formed. A lower tray (210) of staple cartridge (200) retains the staples and staple drivers within cartridge body (202).

Cartridge body (202) of the present example further includes a plurality of upwardly-opening recesses (212, 214, 216) formed in deck (204) and having base surfaces through which staple openings (208) extend. More specifically, on each side of elongate slot (206), deck (204) includes an inner row of triangular recesses (212) each having a medial apex that points transversely away from elongate slot (206); an outer row of triangular recesses (214) each having a medial apex that points transversely toward elongate slot (206); and a middle row of diamond-shaped recesses (216) each having an inner medial apex that points transversely toward elongate slot (206) and an opposed outer medial apex that points transversely away from elongate slot (206). Recesses (212, 214, 216) may cooperate to more securely grip and thereby stabilize clamped tissue during stapling and cutting of the clamped tissue.

Cartridge body (202) of the present example further includes a plurality of elongate tabs (218) projecting laterally outwardly from deck (204) on each lateral side of cartridge body (202). Tabs (218) of the present example are spaced apart from one another in a longitudinal direction, and each tab (218) has a generally rounded rectangular shape. Cartridge body (202) further includes a plurality of attachment openings (220) spaced apart from one longitudinally on each side of elongate slot (206), with each attachment opening (220) being smaller than a staple opening (208) and having a hexagonal shape. In the present version, each tab (218) includes at least one attachment opening (220). Attachment openings (220) may be configured to facilitate releasable attachment of an adjunct, such as adjunct (230), to staple cartridge deck (204).

Adjunct (230) has a plurality of sub-structures in the form of three-dimensional, resiliently compressible (or collapsible) nodules (232) that define a lower portion of adjunct (230) and are integrally connected with one another, via an upper portion (233) of adjunct (230), in a plurality of linear arrays defining a lattice structure having an elongate rectangular shape.

Each nodule (232) of the present example has a generally cuboid shape defining four side surfaces (234), a lower surface (236), and an opening (238) in lower surface (236) that extends along a vertical central axis (A1) of nodule (232) and defines an open, hollow interior of nodule (232). Additionally, each nodule (232) is symmetrical about its centroid along a second axis (A2) of nodule (232) that extends horizontally in a proximal-distal direction parallel to the length of adjunct (230), and along a third axis (A3) of nodule (232) that extends horizontally in a direction traverse to the length of adjunct (230), where each axis (A1, A2, A3) extends through the centroid.

Adjunct (230) may be formed of an elastic, bioabsorbable polymeric material having a suitable degree of elasticity that enables adjunct (230) to compress and resiliently resume its original shape. In the present example, each nodule (232) of adjunct (230) is resiliently compressible in such a manner along at least each of its three axes (A1, A2, A3).

IV. Exemplary Alternative Tissue Fastening Features

In some instances, it may be desirable to provide a thermoformable component, such as an adjunct, with one or more features for fastening layers of tissue to each other in a manner that supplements or replaces staples (80). In addition, or alternatively, it may be desirable for such an adjunct to apply a compression spring force to fastened tissue consistently along the entire length of the adjunct, thereby ensuring a secure seal of tissue having a thickness that varies along a length of the adjunct and end effector (50). For example, replacing staples (80) with such features may enable fastening layers of tissue to each other without requiring deployment of staples (80) from end effector (50). In some cases, this may further enable fastening layers of tissue to each other without the use of various components of end effector (50) associated with staple deployment, such as staple forming pockets (58), staple openings (78), staple drivers (82), and/or wedge sled (86), such that some or all of these components may be omitted. Exemplary versions of such features are described in greater detail below. Unless otherwise described, it will be appreciated that such features may be applied to a multi-layer adjunct similar to buttress assemblies (110, 112) described above in connection with FIGS. 7-9, to a compressible monolithic adjunct similar to adjunct (230) described above in connection with FIGS. 10-12, or to fasteners similar to staples (80).

A. Exemplary Thermally-Bonded Pair of Adjuncts

FIGS. 13A-13C show first and second exemplary compressible unitary (e.g., monolithic) adjuncts (330a, 330b) configured for releasable attachment to a staple cartridge (not shown) similar to staple cartridge (200). Adjuncts (330a, 330b) are configured for use with end effector (50) and are each similar to adjunct (230) described above except as otherwise described below. In this regard, adjuncts (330a, 330b) each have a respective plurality of three-dimensional, resiliently compressible nodules (332a, 332b) that are integrally connected with one another in a plurality of linear arrays defining a lattice structure having an elongate rectangular shape.

More particularly, first adjunct (330a) is configured for releasable attachment to a first jaw (not shown), such as an upper jaw similar to upper jaw (54), and has a plurality of first nodules (332a) (one shown) that define a lower portion of first adjunct (330a) and are integrally connected with one another, via an upper portion (333a) of first adjunct (330a). Each first nodule (332a) of the present example has a generally cuboid shape defining four side surfaces (334a), a lower surface (336a), and an opening (338a) in lower surface (336a) that extends along a vertical central axis (not shown) of first nodule (332a) and defines an open, hollow interior of first nodule (332a). Additionally, each first nodule (332a) is symmetrical about its centroid along a second axis (not shown) of first nodule (332a) that extends horizontally in a proximal-distal direction parallel to the length of first adjunct (330a), and along a third axis (not shown) of first nodule (332a) that extends horizontally in a direction traverse to the length of first adjunct (330a), where each of the three axes extends through the centroid. While a single first nodule (332a) is shown, it will be appreciated that a plurality of first nodules (332a) may be arranged in a plurality of axial rows each extending in a proximal-distal direction, and/or in a plurality of transverse rows each extending in a direction transverse to a length of the staple cartridge, in a manner similar to that shown in FIGS. 10-12. In some versions, first nodules (332a) of each such row may be equally sized and equally spaced apart from each other along their respective rows. First nodules (332a) may thus be arranged periodically on upper portion (333a).

Second adjunct (330b) is configured for releasable attachment to a second jaw (not shown), such as a lower jaw similar to lower jaw (52), and has a plurality of second nodules (332b) (one shown) that define an upper portion of second adjunct (330b) and are integrally connected with one another, via a lower portion (333b) of second adjunct (330b). Each second nodule (332b) of the present example has a generally cuboid shape defining four side surfaces (334b), an upper surface (336b), and an opening (338b) in upper surface (336b) that extends along a vertical central axis (not shown) of second nodule (332b) and defines an open, hollow interior of second nodule (332b). Additionally, each second nodule (332b) is symmetrical about its centroid along a second axis (not shown) of second nodule (332b) that extends horizontally in a proximal-distal direction parallel to the length of second adjunct (330b), and along a third axis (not shown) of second nodule (332b) that extends horizontally in a direction traverse to the length of second adjunct (330b), where each of the three axes extends through the centroid. While a single second nodule (332b) is shown, it will be appreciated that a plurality of second nodules (332b) may be arranged in a plurality of axial rows each extending in a proximal-distal direction, and/or in a plurality of transverse rows each extending in a direction transverse to a length of the staple cartridge, in a manner similar to that shown in FIGS. 10-12. In some versions, second nodules (332b) of each such row may be equally sized and equally spaced apart from each other along their respective rows. Second nodules (332b) may thus be arranged periodically on lower portion (333b). In this regard, the sizing and spacing of second nodules (332b) may be substantially similar (e.g., identical) to the sizing and spacing of first nodules (332a), such that each second nodule (332b) may be configured to align with a corresponding first nodule (332a), as described in greater detail below.

Adjuncts (330a, 330b) may be formed of an elastic, bioabsorbable polymeric material, such as a thermoplastic, having a suitable degree of elasticity that enables each adjunct (330a, 330b) to compress and resiliently resume its original shape. In the present example, each nodule (332a, 332b) of each adjunct (330a, 330b) is resiliently compressible in such a manner along at least each of its three axes. Adjuncts (330a, 330b) of the present example are thermally bondable to each other. More particularly, each first nodule (332a) of first adjunct (330a) is configured to overlie a corresponding second nodule (332b) of second adjunct (330b) such that the respective lower and upper surfaces (336a, 336b) may confront each other to facilitate thermal bonding of each first nodule (332a) to the corresponding second nodule (332b). For example, each first nodule (332a) may be configured to thermally bond with the corresponding second nodule (332b) in response to application of heat to the respective pair of first and second nodules (332a, 332b). In some versions, such application of heat may be accompanied by compressing of the pair of first and second nodules (332a, 332b) against each other to further promote such thermal bonding.

FIGS. 13A-13C show an exemplary sequence in which adjuncts (330a, 330b) are thermally bonded to each other through two opposed layers of tissue ($T_1$, $T_2$), thereby fastening together layers of tissue ($T_1$, $T_2$) while also securing adjuncts (330a, 330b) to the same layers of tissue ($T_1$, $T_2$). In particular, FIG. 13A shows layers of tissue ($T_1$, $T_2$) positioned between adjuncts (330a, 330b), which may be releasably attached to respective jaws (not shown) of an end effector, similar to end effector (50), with one jaw in an open position relative to the other jaw. Layers of tissue ($T_1$, $T_2$) are thus interposed between corresponding pairs of nodules (332a, 332b) of adjuncts (330a, 330b).

Next, the jaws are closed against each other such that layers of tissue ($T_1$, $T_2$) are compressed between the jaws, with adjuncts (330a, 330b) engaging opposite surfaces of tissue layers ($T_1$, $T_2$), as shown in FIG. 13B. More particularly, the respective lower and upper surfaces (336a, 336b) of corresponding pairs of nodules (332a, 332b) confront each other to sandwich portions of tissue layers ($T_1$, $T_2$) therebetween. While tissue layers ($T_1$, $T_2$) are compressed between the corresponding pairs of nodules (332a, 332b), the corresponding pairs of nodules (332a, 332b) are heated. For example, nodules (332a, 332b) may be heated via the application of radiofrequency (RF) energy thereto by respective RF electrodes (340a, 340b), which may be supplied with power by one or more power source(s) (342), as shown in FIG. 13B. In this regard, RF electrodes (340a, 340b) may be configured to cooperate with each other to apply bipolar RF energy to nodules (332a, 332b). For instance, one of RF electrodes (340a) may be configured to serve as an active electrode and the other of RF electrodes (340b) may be configured to serve as a return electrode. In some versions, RF electrodes (340a, 340b) may each be coupled to a respective jaw of the end effector for applying RF energy to the respective nodules (332a, 332b) through the corresponding upper or lower portion (333a, 333b) of the respective adjunct (330a, 330b).

As shown in FIG. 13C, such heating of nodules (332a, 332b) while tissue layers ($T_1$, $T_2$) are compressed therebetween may result in partial ablation of tissue layers ($T_1$, $T_2$) sufficient to allow the confronting, heated surfaces (336a, 336b) of respective pairs of nodules (332a, 332b) to penetrate through tissue layers ($T_1$, $T_2$) into direct engagement with each other and thereby thermally bond each first nodule (332a) to the corresponding second nodule (332b). While RF electrodes (340a, 340b) are shown for heating nodules (332a, 332b) via the application of RF energy in the present example, it will be appreciated that any other suitable energy application device(s) and/or any other suitable type(s) of energy may be used for heating nodules (332a, 332b) to thermally bond nodules (332a, 332b) to each other. In any event, the thermal bonding of nodules (332a, 332b) to each other causes tissue layers ($T_1$, $T_2$) to be captured and compressed between adjuncts (330a, 330b). More particularly, the portions of tissue layers ($T_1$, $T_2$) adjacent to and/or surrounding each thermally-bonded pair of nodules (332a, 332b) may be captured and retained vertically between the upper and lower portions (333a, 333b) of adjuncts (330a, 330b), and may be further captured and retained horizontally between longitudinally-adjacent and/or laterally-adjacent pairs of thermally-bonded pairs of nodules (332a, 332b). Such capturing of tissue layers ($T_1$, $T_2$) between adjuncts (330a, 330b) may fasten tissue layers ($T_1$, $T_2$) to each other while also securing each adjunct (330a, 330b) to the respective tissue layer ($T_1$, $T_2$). In some versions, tissue layers ($T_1$, $T_2$) may be at least partially welded to each other at or near the thermally-bonded nodules (332a, 332b) as a result of tissue layers ($T_1$, $T_2$) being heated during the heating of nodules (332a, 332b) to further secure tissue layers ($T_1$, $T_2$) to each other. In any event, the fastening of tissue layers ($T_1$, $T_2$) to each other achieved via such thermal bonding may be sufficiently secure to avoid the need to staple tissue layers ($T_1$, $T_2$) with staples (80). In addition, or alternatively, the portions of tissue layers ($T_1$, $T_2$) adjacent to and/or surrounding each thermally-bonded pair of nodules (332a, 332b) may be compressed between the upper and lower portions (333a, 333b) of adjuncts (330a, 330b) as a result of the thermal bonding of nodules (332a, 332b) to provide a secure seal between tissue layers ($T_1$, $T_2$).

After thermally-bonding nodules (332a, 332b), the end effector may be pulled away from tissue ($T_1$, $T_2$) to disengage adjuncts (330a, 330b) from the end effector such that adjuncts (330a, 330b) remain secured to tissue ($T_1$, $T_2$) via the thermal bonding of nodules (332a, 332b). It will be appreciated that the thermal bonding of nodules (332a, 332b) may be performed substantially simultaneously with cutting tissue layers ($T_1$, $T_2$), such as via distally presented cutting edge (62) of firing member (60). In this regard, distally presented cutting edge (62) of firing member (60) may also cut through a centerline of adjuncts (330a, 330b), separating each adjunct (330a, 330b) into a corresponding pair of sections, such that each section remains secured to a respective severed region of tissue ($T_1$, $T_2$) in a manner similar to that described above in connection with FIG. 9.

B. Exemplary Fastener with Thermally-Expandable Tips

Figure 14A:
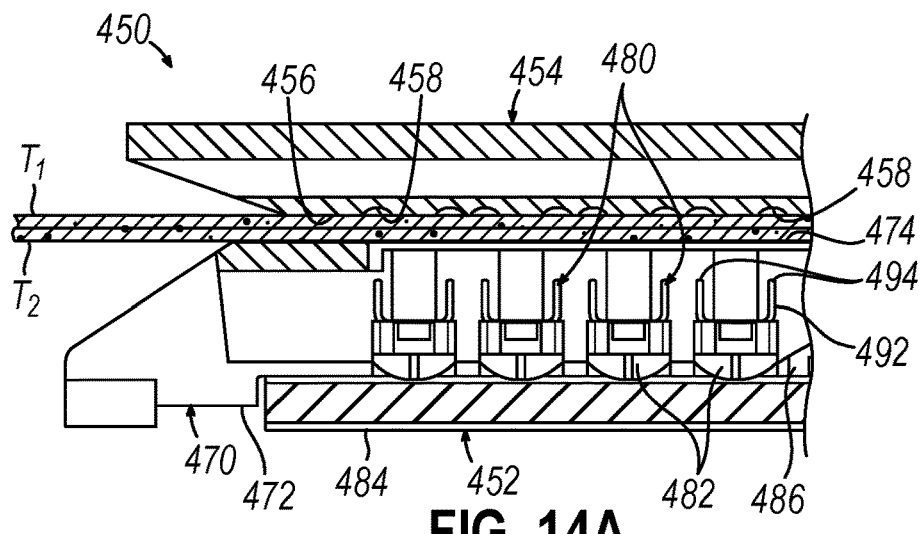
FIG. 14A depicts a side cross-sectional view of another exemplary end effector for use with the surgical stapler of FIG. 1, with tissue layers positioned between upper and lower jaws of the end effector, showing exemplary fasteners having thermally-expandable tips housed within an exemplary fastener cartridge supported by the lower jaw, showing the tips in an undeformed state.
Figure 14B:
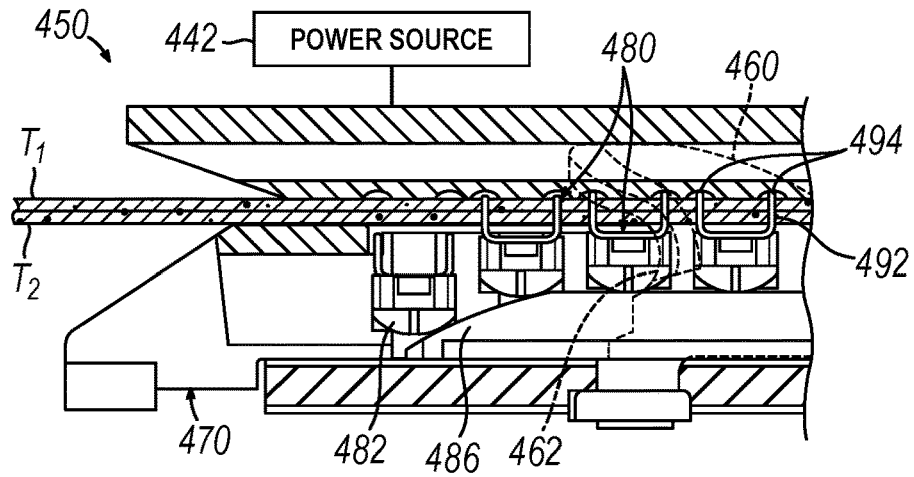
FIG. 14B depicts a side cross-sectional view of the end effector of FIG. 14A, showing deployment of the fasteners through the tissue layers, and further showing heating of the tips of the fasteners within corresponding pockets of the upper jaw.
Figure 14C:
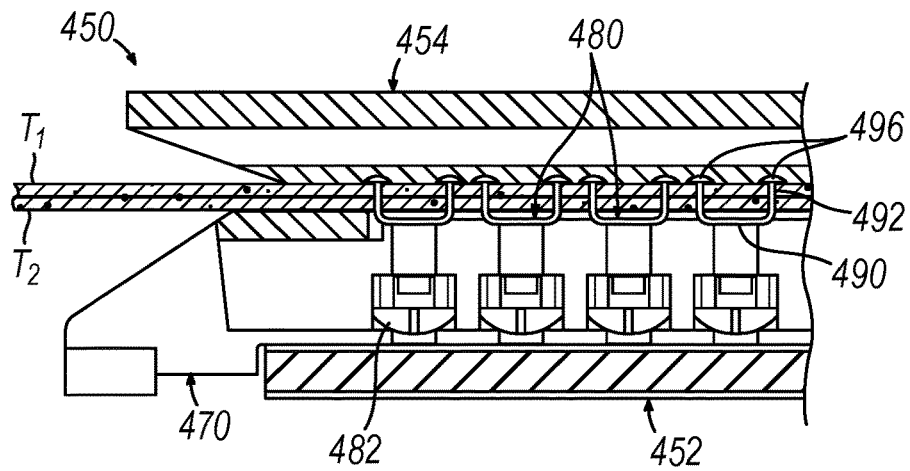
FIG. 14C depicts a side cross-sectional view of the end effector of FIG. 14A, showing the tips of the fasteners thermally expanded to define respective heads for securing the tissue layers to each other.

FIGS. 14A-14C show another exemplary end effector (450) configured to clamp and cut tissue, as well as to fasten such tissue via exemplary fasteners (480). End effector (450) and fasteners (480) are configured for use with surgical stapler (10) and are similar to end effector (50) and staples (80) described above except as otherwise described below. In this regard, end effector (450) includes a lower jaw (452) that supports a fastening assembly in the form of a replaceable fastener cartridge (470), and an upper jaw (454) that presents an anvil (456) having a plurality of fastener tip forming pockets (458). Upper jaw (454) is configured to pivot relative to lower jaw (452) to clamp tissue between fastener cartridge (470) and anvil (456) and subsequently form fasteners (480) deployed by fastener cartridge (470). End effector (450) further includes an elongate firing member (460) configured to translate distally through end effector (450) to drive fasteners (480) from fastener cartridge (470) toward anvil (456) and simultaneously cut tissue with a distally presented cutting edge (462).

Fastener cartridge (470) is similar to staple cartridge (70) described above except as otherwise described below. In this regard, fastener cartridge (470) includes a cartridge body (472) having an upwardly facing deck (474), an elongate slot (not shown) similar to slot (76) extending along a central axis of cartridge body (472) and opening upwardly through deck (474), and a plurality of fastener openings (not shown) similar to staple openings (78) extending through deck (474) on each side of the elongate slot. Each fastener opening slidably houses an unformed fastener (480) and a respective fastener driver (482) positioned beneath fastener (480). A lower tray (484) encloses an underside of cartridge body (472) and thereby retains fasteners (480) and fastener drivers (482) within cartridge body (472). A wedge sled (486) is slidably disposed within cartridge body (472) and includes upwardly presented cam surfaces configured to engage the undersides of fastener drivers (482).

Each fastener (480) of the present example includes an elongate crown (490) and a pair of legs (492) extending upwardly and generally perpendicularly from respective ends of crown (490) to respective tips (494). In the example shown, each tip (494) is thermally deformable from a sharp, undeformed state (FIGS. 14A-14B) in which tip (494) is configured to pierce tissue to an expanded (e.g., widened), deformed state (FIG. 14C) in which tip (494) defines a generally mushroom-shaped, rivet-like head (496) that extends radially outwardly relative to the respective leg (492) for sandwiching one or more tissue layers ($T_1$, $T_2$) against the corresponding crown (490) to thereby secure the respective fastener (480) to such tissue layers ($T_1$, $T_2$). In this regard, each fastener (480) may be formed of a bioabsorbable polymeric material, such as a thermoplastic. In some versions, each fastener (480) may be formed of nylon.

FIGS. 14A-14C show an exemplary sequence in which end effector (450) is actuated to drive fasteners (480) through two opposed layers of tissue ($T_1$, $T_2$). In particular, FIG. 14A shows layers of tissue ($T_1$, $T_2$) positioned between anvil (456) and fastener cartridge (470), with anvil (456) closed against fastener cartridge (470) such that layers of tissue ($T_1$, $T_2$) are compressed between anvil (456) and staple cartridge (470).

End effector (450) is then fired as shown in FIG. 14B, with firing member (460) actuated distally through end effector (450) such that a distal end of firing member (460) drives wedge sled (486) distally to cam fastener drivers (482) upwardly and thereby drive the respective fasteners (480) outwardly from the fastener openings. Legs (492) of fasteners (480) pass through the clamped tissue layers ($T_1$, $T_2$) such that the respective tips (494) are each received within corresponding fastener tip forming pockets (458) of anvil (456). Tips (494) are then heated and thereby thermally deformed within fastener tip forming pockets (458) of anvil (456) from the sharp, undeformed state to the widened, deformed state to define rivet-like heads (496). Simultaneously, the clamped tissue is severed by cutting edge (462) of firing member (460). In some versions, tips (494) may be heated via thermal activation of anvil (456) by a power source (442) from a relatively low temperature to a relatively high temperature sufficient to thermally deform tips (494) within fastener tip forming pockets (458) of anvil (456). In addition, or alternatively, one or more heating elements or any other suitable energy application device(s) may be coupled to anvil (456) for heating fastener tip forming pockets (458) and tips (494) therein. For example, fastener tip forming pockets (458) may be heated via the application of radiofrequency (RF) energy thereto. In some versions, each rivet-like head (496) may have a shape similar (e.g., complementary) to that of the corresponding fastener tip forming pockets (458).

As shown in FIG. 14C, heads (496) of driven fasteners (480) capture and retain tissue layers ($T_1$, $T_2$) against the respective crowns (490). In addition, or alternatively, tissue layers ($T_1$, $T_2$) may be compressed between heads (496) and crowns (490) of fasteners (480) to provide a secure seal between tissue layers ($T_1$, $T_2$). While not shown, one or more buttress assemblies and/or compressible adjuncts similar to those described above may be captured and retained against tissue layers ($T_1$, $T_2$) by heads (496) and/or crowns (490) of fasteners (480), such as to provide structural reinforcement to the lines of fasteners (480) formed in tissue ($T_1$, $T_2$).

C. Exemplary Fastener with Mechanically-Expandable Legs

FIGS. 15A-15C show another exemplary fastener (580) configured for fastening together layers of tissue. Fastener (580) is configured for use with end effector (50) and is similar to staples (80) described above except as otherwise described below. In this regard, fastener (580) of the present example includes an elongate crown (590) and a pair of legs (592) extending upwardly and generally perpendicularly from respective ends of crown (590) to respective sharp tips (594) configured to pierce tissue. In the example shown, each leg (592) is mechanically (e.g., plastically) deformable from a narrow, undeformed state (FIG. 15A) in which leg (592) is configured to pass through tissue pierced by the respective tip (594) to an expanded (e.g., widened), deformed state (FIGS. 15B-15C) in which a portion of leg (592) near the respective tip (594) defines a generally X-shaped, molly-like anchor (596) that extends radially outwardly relative to a remainder of the respective leg (592) for sandwiching two or more tissue layers ($T_1$, $T_2$) against the corresponding crown (590) to thereby secure the respective fastener (580) to such tissue layers ($T_1$, $T_2$). In this regard, each fastener (580) may be formed of a bioabsorbable polymeric material, and includes a circumferential array of elongate slots (598) extending through each of the respective legs (592) near the corresponding tips (594) to promote a controlled, partial collapse of each leg (592) in a predetermined manner to deploy anchors (596) in response to the corresponding tips (594) being driven against a hard stop, such as that provided by staple forming pockets (58) of anvil (56).

FIGS. 15A-15C show an exemplary sequence in which fastener (580) is driven through at least two layers of tissue ($T_1$, $T_2$). In particular, FIG. 15A shows a leg (592) of fastener (580) in the narrow, undeformed state, and FIG. 15B shows the leg (592) being driven upwardly, such as via drivers similar to staple drivers (82), through clamped tissue (not shown) against a corresponding pocket (558) of an anvil (556) and thereby deformed from the narrow, undeformed state to the widened, deformed state to deploy anchor (596). Simultaneously, the clamped tissue is severed, such as by cutting edge (62) of firing member (60). As shown in FIG. 15C, anchors (596) of driven fastener (580) capture and retain tissue layers ($T_1$, $T_2$) against crown (590). In addition, or alternatively, tissue layers ($T_1$, $T_2$) may be compressed between anchors (596) and crown (590) of fastener (580) to provide a secure seal between tissue layers ($T_1$, $T_2$). While not shown, one or more buttress assemblies and/or compressible adjuncts similar to those described above may be captured and retained against tissue layers ($T_1$, $T_2$) by anchors (596) and/or crown (590) of fastener (580), such as to provide structural reinforcement to the lines of multiple fasteners (580) formed in tissue ($T_1$, $T_2$).

D. Exemplary Fastener with Variably-Angled Bar Having Sharp Tip

Figure 16:
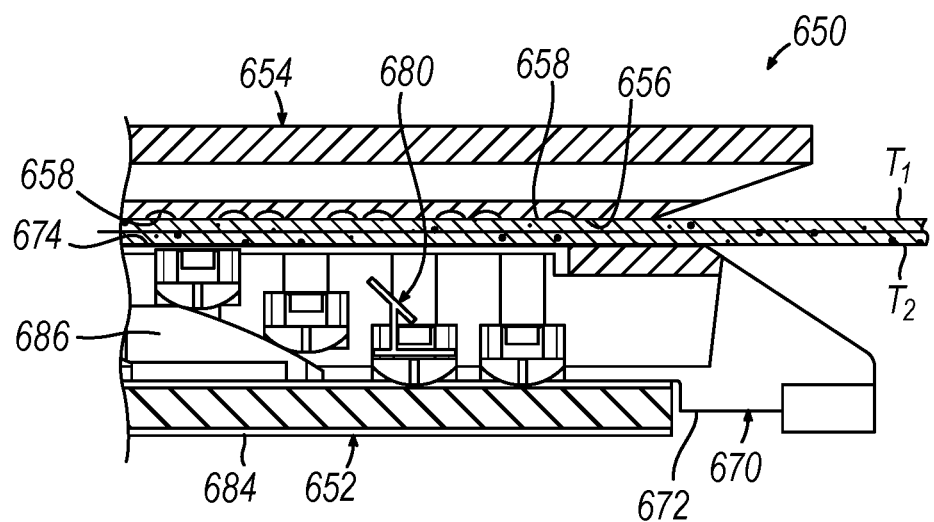
FIG. 16 depicts a side cross-sectional view of another exemplary end effector for use with the surgical stapler of FIG. 1, with at least one tissue layer positioned between upper and lower jaws of the end effector, showing an exemplary fastener having a variably-angled bar housed within an exemplary fastener cartridge supported by the lower jaw.
Figure 17:
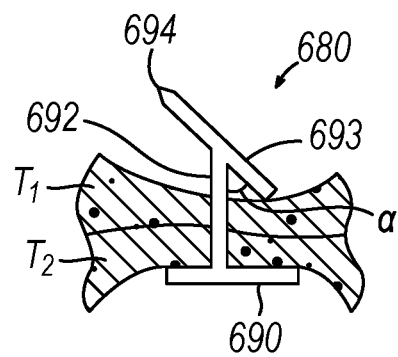
FIG. 17 depicts a side elevational view of the fastener of FIG. 16, showing the variably-angled bar assuming a first angle relative to a leg of the fastener for capturing at least one tissue layer having a first thickness.
Figure 18:
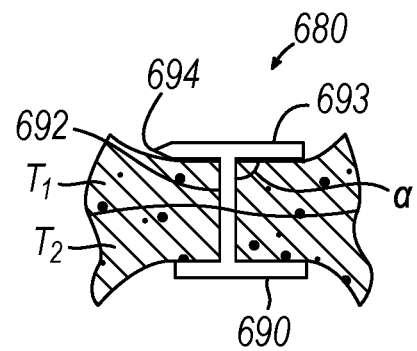
FIG. 18 depicts a side elevational view of the fastener of FIG. 16, showing the variably-angled bar assuming a second angle relative to a leg of the fastener greater than the first angle for capturing at least one tissue layer having a second thickness greater than the first thickness.

FIGS. 16-18 show another exemplary end effector (650) configured to clamp and cut tissue, as well as to fasten such tissue via exemplary fasteners (680) (one shown). End effector (650) and fasteners (680) are configured for use with surgical stapler (10) and are similar to end effector (50) and staples (80) described above except as otherwise described below. In this regard, end effector (650) includes a lower jaw (652) that supports a fastening assembly in the form of a replaceable fastener cartridge (670), and an upper jaw (654) that presents an anvil (656) having a plurality of fastener tip forming pockets (658). Fastener cartridge (670) is similar to staple cartridge (70) described above except as otherwise described below. In this regard, fastener cartridge (670) includes a cartridge body (672) having an upwardly facing deck (674) and a plurality of fastener openings (not shown) similar to staple opening (78) extending through deck (674). Each fastener opening slidably houses an unformed fastener (680) and a respective fastener driver (682) positioned beneath fastener (680). A lower tray (684) encloses an underside of cartridge body (672). A wedge sled (686) is slidably disposed within cartridge body (672) and includes upwardly presented cam surfaces configured to engage the undersides of fastener drivers (682).

Each fastener (680) of the present example includes an elongate crown (690) and a single leg (692) extending upwardly and generally perpendicularly from a position along crow (690) between the ends of crown (690) to a variably-angled bar (693) having a sharp tip (694) configured to pierce tissue. In the example shown, bar (693) and leg (692) are each configured to pass through tissue pierced by tip (694), and bar (693) is further configured to assume an angle ($\alpha$) relative to leg (692) sufficiently great to sandwich two or more tissue layers ($T_1$, $T_2$) against crown (690) to thereby secure fastener (680) to such tissue layers ($T_1$, $T_2$). In this regard, bar (693) may be configured to assume an angle ($\alpha$) of between about 20° and about 90° relative to leg (692). For example, bar (693) may be configured to assume an angle ($\alpha$) of about 20° relative to leg (692) to capture and retain a relatively thin pair of tissue layers ($T_1$, $T_2$) against crown (690), as shown in FIG. 17. In addition, or alternatively, bar (693) may be configured to assume an angle ($\alpha$) of about 90° relative to leg (692) to capture and retain a relatively thick pair of tissue layers ($T_1$, $T_2$) against crown (690), as shown in FIG. 18.

E. Exemplary Tissue Clip with Flat Clamping Surfaces

Figure 19A:
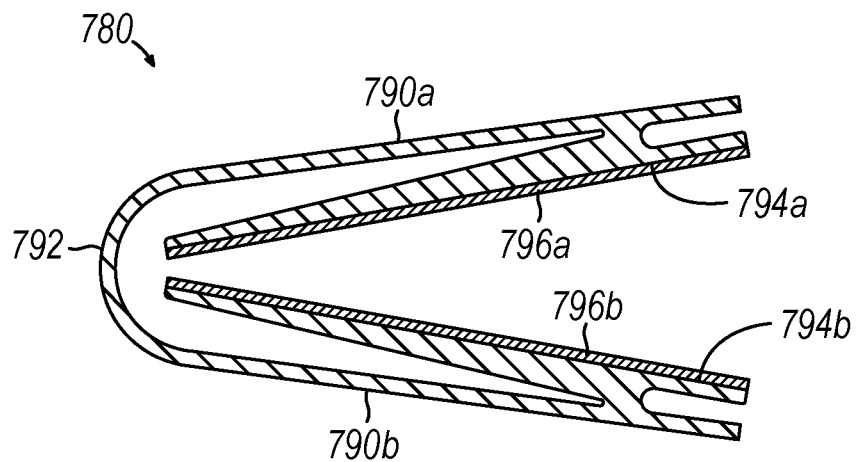
FIG. 19A depicts a side cross-sectional view of an exemplary tissue clip with flat clamping surfaces, showing the tissue clip in an open state.
Figure 19B:
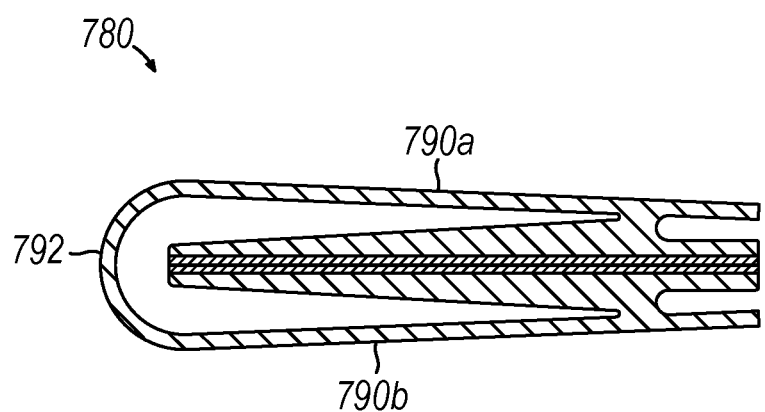
FIG. 19B depicts a side cross-sectional view of the tissue clip of FIG. 19A, showing the tissue clip in a closed state.

FIGS. 19A-19B show an exemplary clip (780) configured for clamping together layers of tissue. In this regard, clip (780) of the present example includes upper and lower clip arms (790a, 790b) each extending distally from a living hinge (792) such that clip arms (790a, 790b) are pivotable relative to each other between an open state (FIG. 19A) and a closed state (FIG. 19B). In the example shown, upper and lower clip arms (790a, 790b) include flat upper and lower clamping surfaces (794a, 794b), respectively, configured to receive tissue therebetween. For example, one or more layers of tissue (not shown) may be positioned between clamping surfaces (794a, 794b) while clip (780) is in the open state, and such tissue may be compressed by clamping surfaces (794a, 794b) while clip (780) is in the closed state. In some versions, clip (780) may be resiliently biased toward the closed state to promote compression of tissue by clamping surfaces (794a, 794b) in the absence of external forces acting upon clip arms (790a, 790b).

As shown, upper and lower cushions (796a, 796b) may be secured to upper and lower clamping surfaces (794a, 794b), respectively, for applying a compression spring force to the tissue consistently along the entire length of clip (780), thereby ensuring a secure seal of tissue having a thickness that varies along the length of the clip (780). In this regard, clip (780) may have a length equal to or greater than that of a cut line through the tissue, such that a first clip (780) may clamp together the tissue layers on a first side of the tissue transection and a second clip (780) may clamp together the tissue layers on a second side of the tissue transection, thereby eliminating the need for staples (80) or other fasteners to seal the tissue.

F. Exemplary Tissue Clip with Mating Clamping Surfaces

Figure 20:
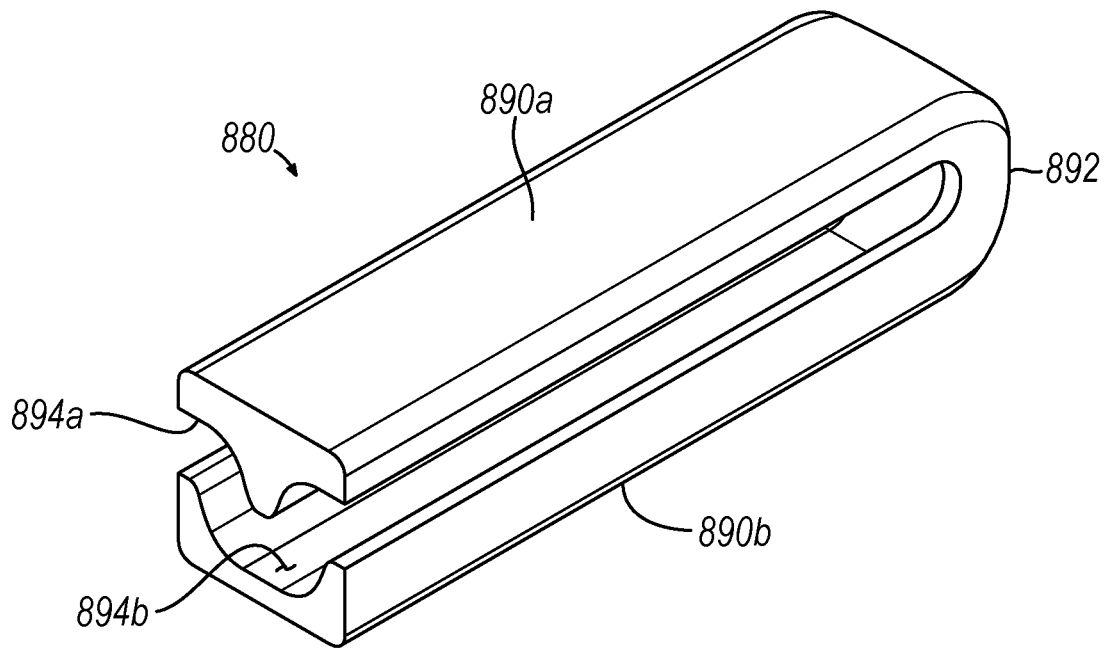
FIG. 20 depicts a perspective view of another exemplary tissue clip with mating clamping surfaces.
Figure 21:
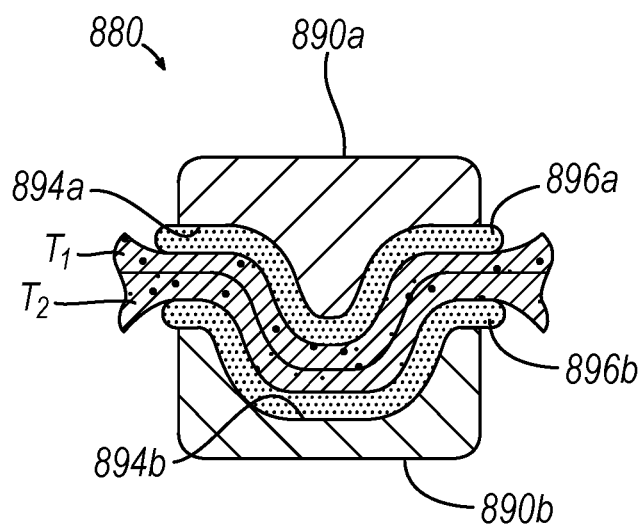
FIG. 21 depicts a cross-sectional end view of the tissue clip of FIG. 20, showing at least one tissue layer captured between the mating clamping surfaces.

FIGS. 20-21 show another exemplary clip (880) configured for clamping together layers of tissue. In this regard, clip (880) of the present example includes upper and lower clip arms (890a, 890b) each extending distally from a living hinge (892) such that clip arms (890a, 890b) are pivotable relative to each other between an open state (not shown) and the illustrated closed state. In the example shown, upper and lower clip arms (890a, 890b) include curved upper and lower clamping surfaces (894a, 894b), respectively, configured to receive tissue therebetween. For example, two or more layers of tissue ($T_1$, $T_2$) may be positioned between clamping surfaces (894a, 894b) while clip (880) is in the open state, and such tissue ($T_1$, $T_2$) may be compressed by clamping surfaces (894a, 894b) while clip (880) is in the closed state. In some versions, clip (880) may be resiliently biased toward the closed state to promote compression of tissue ($T_1$, $T_2$) by clamping surfaces (894a, 894b) in the absence of external forces acting upon clip arms (890a, 890b). In the example shown, clamping surfaces ((894a, 894b) are each curved downwardly in a plane perpendicular to a longitudinal axis of clip (880) such that lower clamping surface (894b) defines a generally U-shaped longitudinal channel and upper clamping surface (894) defines a generally U-shaped longitudinal protrusion configured to mate therewith when clip (880) is in the closed state to promote alignment of clip arms (890a, 890b) and inhibit slippage of clamping surfaces (894a, 894b) off of tissue ($T_1$, $T_2$).

As shown in FIG. 21, upper and lower cushions (896a, 896b) may be secured to upper and lower clamping surfaces (894a, 894b), respectively, for applying a compression spring force to the tissue ($T_1$, $T_2$) consistently along the entire length of clip (880), thereby ensuring a secure seal of tissue ($T_1$, $T_2$) having a thickness that varies along the length of the clip (880). In this regard, clip (880) may have a length equal to or greater than that of a cut line through the tissue ($T_1$, $T_2$), such that a first clip (880) may clamp together the tissue layers ($T_1$, $T_2$) on a first side of the tissue transection and a second clip (880) may clamp together the tissue layers ($T_1$, $T_2$) on a second side of the tissue transection, thereby eliminating the need for staples (80) or other fasteners to seal the tissue ($T_1$, $T_2$).

G. Exemplary Tissue Clip with Locking Elements

Figure 22:
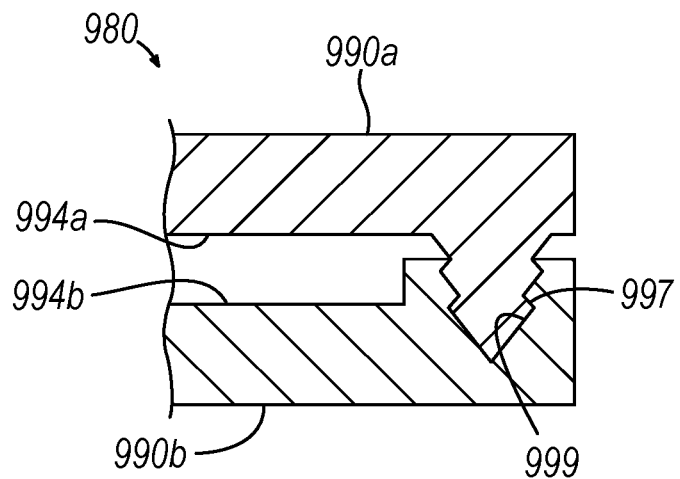
FIG. 22 depicts a partial side cross-sectional view of another exemplary tissue clip with locking elements.

FIG. 22 shows a distal portion of another exemplary clip (980) configured for clamping together layers of tissue. In this regard, clip (980) of the present example includes upper and lower clip arms (990a, 990b) each extending distally from a living hinge (not shown) such that clip arms (990a, 990b) are pivotable relative to each other between an open state (not shown) and the illustrated closed state. In the example shown, upper and lower clip arms (990a, 990b) include flat upper and lower clamping surfaces (994a, 994b), respectively, configured to receive tissue therebetween. For example, one or more layers of tissue (not shown) may be positioned between clamping surfaces (994a, 994b) while clip (980) is in the open state, and such tissue may be compressed by clamping surfaces (994a, 994b) while clip (980) is in the closed state. In some versions, clip (980) may be resiliently biased toward the closed state to promote compression of tissue by clamping surfaces (994a, 994b) in the absence of external forces acting upon clip arms (990a, 990b). In the example shown, upper clip arm (990a) includes a distal barbed pin (997) configured to pierce through the compressed tissue and lower clip arm (990b) includes a distal receptacle (999) configured to securely capture distal barbed pin (997) for selectively locking clip (980) in the closed state and thereby promote a reliable clamping force upon the compressed tissue.

H. Exemplary Tissue Patch with Barbed Members

Figure 23:
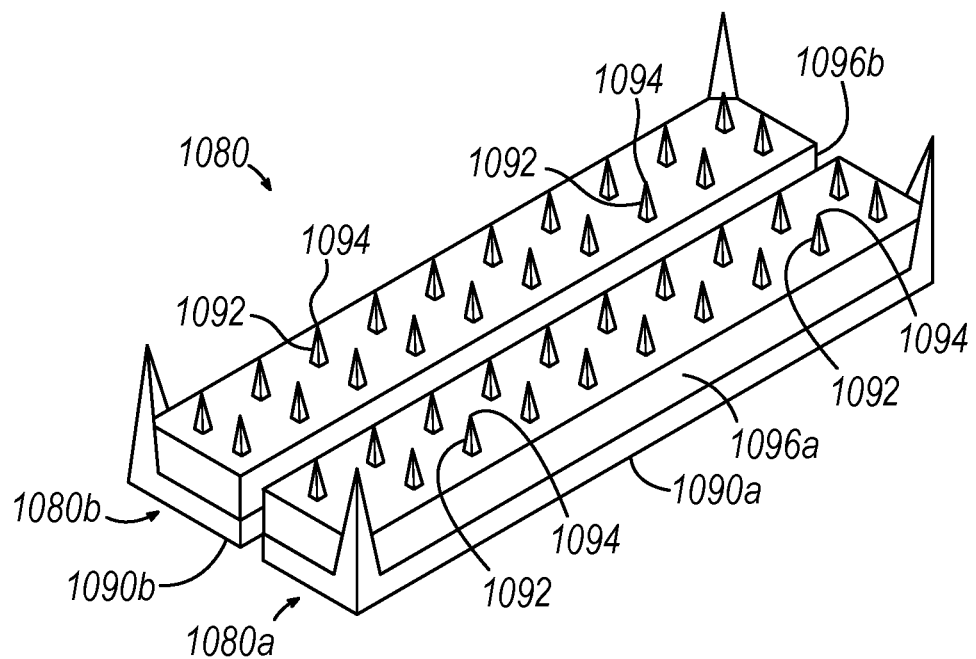
FIG. 23 depicts a perspective view of an exemplary tissue patch with barbed members.

FIG. 23 shows a distal portion of an exemplary patch (1080) configured for fastening together layers of tissue. In this regard, patch (1080) of the present example may be releasably attached to a respective jaw of an end effector, similar to end effector (50), and includes a pair of lateral patch sections (1080a, 1080b) configured for placement on respective sides of a staple cartridge slot, similar to staple cartridge slot (76), each including a respective flexible membrane (1090a, 1090b) having a plurality of barbed members (1092) extending upwardly therefrom to respective sharp tips (1094) configured to pierce tissue. In this manner, barbed members (1092) may capture and retain the pierced tissue against the respective flexible membrane (1090a, 1090b). In the example shown, lateral patch sections (1080a, 1080b) also include corresponding cushions (1096a, 1096b) secured to the respective flexible membranes (1090a, 1090b) (e.g., via the respective barbed members (1092) for applying a compression spring force to the tissue consistently along the entire length of patch (1080), thereby ensuring a secure seal of tissue having a thickness that varies along the length of the patch (1080) and eliminating the need for staples (80) or other fasteners to seal the tissue.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus configured for use with an end effector of a surgical fastening instrument, comprising: (a) a first adjunct including a plurality of first resiliently compressible elements interconnected with each other; and (b) a second adjunct opposed from the first adjunct, the second adjunct including a plurality of second resiliently compressible elements interconnected with each other, wherein each first resiliently compressible element of the plurality of first resiliently compressible elements is configured to align and thermally bond with a corresponding second resiliently compressible element of the plurality of second resiliently compressible elements to secure the first and second adjuncts to each other.

Example 2

The apparatus of Example 1, wherein the plurality of first resiliently compressible elements are integrally formed together with each other as a unitary piece.

Example 3

The apparatus of any one or more of Examples 1 through 2, wherein the plurality of second resiliently compressible elements are integrally formed together with each other as a unitary piece.

Example 4

The apparatus of any one or more of Examples 1 through 3, wherein the plurality of first resiliently compressible elements includes a plurality of first resiliently compressible nodules, wherein the plurality of second resiliently compressible elements includes a plurality of second resiliently compressible nodules.

Example 5

The apparatus of any one or more of Examples 1 through 4, wherein each first resiliently compressible element of the plurality of first resiliently compressible elements and each second resiliently compressible element of the plurality of second resiliently compressible elements includes a bioabsorbable thermoplastic material.

Example 6

The apparatus of any one or more of Examples 1 through 5, wherein the plurality of first resiliently compressible elements and the plurality of second resiliently compressible elements are each arranged periodically.

Example 7

The apparatus of any one or more of Examples 1 through 6, wherein each first resiliently compressible element of the plurality of first resiliently compressible elements is configured to thermally bond with the corresponding second resiliently compressible element of the plurality of second resiliently compressible elements in response to application of heat thereto.

Example 8

The apparatus of Example 7, wherein each first resiliently compressible element of the plurality of first resiliently compressible elements is configured to be compressed with the corresponding second resiliently compressible element of the plurality of second resiliently compressible elements during the application of heat thereto.

Example 9

The apparatus of any one or more of Examples 1 through 8, wherein each first resiliently compressible element of the plurality of first resiliently compressible elements includes a first surface, wherein each second resiliently compressible element of the plurality of second resiliently compressible elements includes a second surface configured to confront the first surface of the corresponding first resiliently compressible element when aligned therewith.

Example 10

The apparatus of any one or more of Examples 1 through 9, wherein each first resiliently compressible element of the plurality of first resiliently compressible elements is thermally bonded with the corresponding second resiliently compressible element of the plurality of second resiliently compressible elements.

Example 11

A surgical fastening instrument, comprising: (a) an end effector including: (i) a first clamping surface, and (ii) a second clamping surface configured to cooperate with the first clamping surface to clamp tissue; and (b) the apparatus of any one or more of Examples 1 through 10, wherein the first adjunct is releasably secured to the first clamping surface, wherein the second adjunct is releasably secured to the second clamping surface.

Example 12

The surgical fastening instrument of Example 11, wherein the end effector further includes at least one heat source configured to apply heat to at least one of the plurality of first resiliently compressible elements or the plurality of second resiliently compressible elements for thermally bonding each first resiliently compressible element of the plurality of first resiliently compressible elements with the corresponding second resiliently compressible element of the plurality of second resiliently compressible elements.

Example 13

The surgical fastening instrument of Example 12, wherein the at least one heat source includes at least one radiofrequency (RF) electrode.

Example 14

The surgical fastening instrument of Example 13, wherein the at least one RF electrode includes a first RF electrode and a second RF electrode configured to cooperate with each other to apply bipolar RF energy to the plurality of first resiliently compressible elements and to the plurality of second resiliently compressible elements.

Example 15

The surgical fastening instrument of Example 14, wherein the first RF electrode is coupled to the first clamping surface, wherein the second RF electrode is coupled to the second clamping surface.

Example 16

A surgical fastening instrument comprising: (a) an end effector including: (i) a first jaw having a plurality of fastener tip forming features, and (ii) a second jaw, wherein the first and second jaws are operable to clamp tissue therebetween; and (b) a fastening assembly supported by the second jaw of the end effector, wherein the fastening assembly includes a plurality of fasteners having a plurality of thermally-deformable tips, wherein the plurality of fasteners is configured to be driven toward the first jaw for positioning the plurality of proximate to corresponding fastener tip forming features of the plurality of fastener tip forming features, wherein each fastener tip forming feature of the plurality of fastener tip forming features is configured to thermally deform the corresponding tip of the plurality of tips.

Example 17

The surgical fastening instrument of Example 16, wherein each fastener tip forming feature of the plurality of fastener tip forming features is configured to thermally deform the corresponding tip of the plurality of tips from a sharp state to an expanded state, wherein each tip of the plurality of tips is configured to pierce the clamped tissue when in the sharp state, wherein each tip of the plurality of tips is configured to define a head for securing the respective fastener to the clamped tissue when in the expanded state.

Example 18

The surgical fastening instrument of any one or more of Examples 16 through 17, wherein the end effector further includes at least one heat source configured to apply heat to each fastener tip forming feature of the plurality of fastener tip forming features for thermally deforming each tip of the plurality of tips.

Example 19

A fastening element configured for use with an end effector of a surgical instrument, comprising: (a) an elongate crown extending between first and second ends; and (b) first and second legs extending generally perpendicularly from the first and second ends, respectively, to first and second tips, respectively, wherein each tip of the first and second tips is thermally deformable from a sharp state in which the respective tip is configured to pierce tissue, to an expanded state in which the respective tip is configured to define a head for securing the fastening element to the pierced tissue.

Example 20

A fastening assembly configured for use with an end effector of a surgical fastening instrument, comprising: (a) a body configured to be supported by a jaw of the end effector; and (b) a plurality of the fastening elements of Example 19 slidably housed within the body.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/704,075, entitled "Tissue Cushion Adjuncts for Surgical Stapler End Effector," filed on Mar. 25, 2022, published as U.S. Pub. No. 2023/0301656 on Sep. 28, 2022; U.S. patent application Ser. No. 17/704,079, entitled "Tissue Cushion Adjunct for Surgical Stapler End Effector," filed on Mar. 25, 2022, published as U.S. Pub. No. 2023/0301674 on Sep. 28, 2022; U.S. patent application Ser. No. 17/704,083, entitled "Tissue Cushion Adjunct With Staple Leg Support Features for Surgical Stapler End Effector," filed on Mar. 25, 2022, published as U.S. Pub. No. 2023/0320742 on Oct. 12, 2022; and U.S. patent application Ser. No. 17/704,094, entitled "Surgical Stapler Features for Stapling Variable Thickness Tissue," filed on Mar. 25, 2022, published as U.S. Pub. No. 2023/0301675 on Sep. 28, 2022. The disclosure of each of these U.S. patent references is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical fastening instrument, comprising:
   (a) an end effector including:
      (i) a first clamping surface, and
      (ii) a second clamping surface configured to cooperate with the first clamping surface to clamp tissue; and
   (b) an apparatus, comprising:
      (i) a first adjunct including a plurality of first resiliently compressible thermoplastic elements interconnected with each other; and
      (ii) a second adjunct opposed from the first adjunct, the second adjunct including a plurality of second resiliently compressible thermoplastic elements interconnected with each other,
      wherein a first sizing and a first spacing of the plurality of first resiliently compressible elements are substantially the same as a second sizing and a second spacing, respectively, of the plurality of second resiliently compressible elements, such that each first resiliently compressible element of the plurality of first resiliently compressible elements is configured to align with a corresponding second resiliently compressible element of the plurality of second resiliently compressible elements, and
      wherein each first resiliently compressible element of the plurality of first resiliently compressible elements is configured to thermally bond with the corresponding second resiliently compressible element of the plurality of second resiliently compressible elements in response to application of heat thereto from at least one heat source to secure the first and second adjuncts to each other,
   wherein the first adjunct is releasably secured to the first clamping surface, wherein the second adjunct is releasably secured to the second clamping surface.

2. The surgical fastening instrument of claim 1, wherein the plurality of first resiliently compressible elements are integrally formed together with each other as a unitary piece.

3. The surgical fastening instrument of claim 1, wherein the plurality of second resiliently compressible elements are integrally formed together with each other as a unitary piece.

4. The surgical fastening instrument of claim 1, wherein the plurality of first resiliently compressible elements includes a plurality of first resiliently compressible nodules, wherein the plurality of second resiliently compressible elements includes a plurality of second resiliently compressible nodules.

5. The surgical fastening instrument of claim 1, wherein each first resiliently compressible element of the plurality of first resiliently compressible elements and each second resiliently compressible element of the plurality of second resiliently compressible elements includes a bioabsorbable thermoplastic material.

6. The surgical fastening instrument of claim 1, wherein the plurality of first resiliently compressible elements and the plurality of second resiliently compressible elements are each arranged periodically.

7. The surgical fastening instrument of claim 1, wherein each first resiliently compressible element of the plurality of first resiliently compressible elements is configured to be compressed with the corresponding second resiliently compressible element of the plurality of second resiliently compressible elements during the application of heat thereto.

8. The surgical fastening instrument of claim 1, wherein each first resiliently compressible element of the plurality of first resiliently compressible elements includes a first surface, wherein each second resiliently compressible element of the plurality of second resiliently compressible elements includes a second surface configured to confront the first surface of the corresponding first resiliently compressible element when aligned therewith.

9. The surgical fastening instrument of claim 1, wherein each first resiliently compressible element of the plurality of first resiliently compressible elements is thermally bonded with the corresponding second resiliently compressible element of the plurality of second resiliently compressible elements.

10. The surgical fastening instrument of claim 1, wherein the plurality of first resiliently compressible elements are equally sized and equally spaced apart from each other along respective first rows, wherein the plurality of second resiliently compressible elements are equally sized and equally spaced apart from each other along respective second rows.

11. The surgical fastening instrument of claim 1, wherein the end effector further includes the at least one heat source configured to apply heat to at least one of the plurality of first resiliently compressible elements or the plurality of second resiliently compressible elements for thermally bonding each first resiliently compressible element of the plurality of first resiliently compressible elements with the corresponding second resiliently compressible element of the plurality of second resiliently compressible elements.

12. The surgical fastening instrument of claim 11, wherein the at least one heat source includes at least one radiofrequency (RF) electrode.

13. The surgical fastening instrument of claim 12, wherein the at least one RF electrode includes a first RF electrode and a second RF electrode configured to cooperate with each other to apply bipolar RF energy to the plurality of first resiliently compressible elements and to the plurality of second resiliently compressible elements.

14. The surgical fastening instrument of claim 13, wherein the first RF electrode is coupled to the first clamping surface, wherein the second RF electrode is coupled to the second clamping surface.

15. An apparatus configured for use with an end effector of a surgical fastening instrument, comprising:

(a) a first adjunct including a plurality of first resiliently compressible nodules interconnected with each other, wherein each first resiliently compressible nodule of the plurality of first resiliently compressible nodules includes a bioabsorbable thermoplastic material, wherein the first adjunct is configured to be releasably secured to a first jaw of the end effector; and (b) a second adjunct opposed from the first adjunct, the second adjunct including a plurality of second resiliently compressible nodules interconnected with each other, wherein each second resiliently compressible nodule of the plurality of second resiliently compressible nodules includes a bioabsorbable thermoplastic material, wherein the second adjunct is configured to be releasably secured to a second jaw of the end effector for accommodating tissue between the first and second adjuncts, wherein a first sizing and a first spacing of the plurality of first resiliently compressible nodules are substantially the same as a second sizing and a second spacing, respectively, of the plurality of second resiliently compressible nodules, such that each first resiliently compressible nodule of the plurality of first resiliently compressible nodules is configured to align with a corresponding second resiliently compressible nodule of the plurality of second resiliently compressible nodules, and wherein each first resiliently compressible nodule of the plurality of first resiliently compressible nodules is configured to thermally bond with the corresponding second resiliently compressible nodule of the plurality of second resiliently compressible nodules in response to application of heat thereto from at least one heat source to secure the first and second adjuncts to each other.

16. The apparatus of claim 15, wherein each first resiliently compressible nodule of the plurality of first resiliently compressible nodules includes a first surface, wherein each second resiliently compressible nodule of the plurality of second resiliently compressible nodules includes a second surface configured to confront the first surface of the corresponding first resiliently compressible nodule when aligned therewith.

17. The apparatus of claim 16, wherein each first resiliently compressible nodule of the plurality of first resiliently compressible nodules includes a first opening in the respective first surface, wherein each second resiliently compressible nodule of the plurality of second resiliently compressible nodules includes a second opening in the respective second surface.

18. An apparatus configured for use with an end effector of a surgical fastening instrument, comprising:

(a) a first adjunct including a plurality of first resiliently compressible thermoplastic nodules interconnected with each other, wherein the plurality of first resiliently compressible nodules are arranged periodically; and (b) a second adjunct opposed from the first adjunct, the second adjunct including a plurality of second resiliently compressible thermoplastic nodules interconnected with each other, wherein the plurality of second resiliently compressible nodules are arranged periodically, wherein the first and second adjuncts are configured to sandwich tissue therebetween, wherein a first sizing and a first spacing of the plurality of first resiliently compressible nodules are substantially the same as a second sizing and a second spacing, respectively, of the plurality of second resiliently compressible nodules, such that each first resiliently compressible nodule of the plurality of first resiliently compressible nodules is configured to align with a corresponding second resiliently compressible nodule of the plurality of second resiliently compressible nodules, and wherein each first resiliently compressible nodule of the plurality of first resiliently compressible nodules is configured to thermally bond with the corresponding second resiliently compressible nodule of the plurality of second resiliently compressible nodules in response to application of heat thereto from at least one heat source to secure the first and second adjuncts to each other.

19. The apparatus of claim 18, wherein each first resiliently compressible nodule of the plurality of first resiliently compressible nodules and each second resiliently compressible nodule of the plurality of second resiliently compressible nodules includes a bioabsorbable thermoplastic material.

20. The apparatus of claim 18, wherein the first and second adjuncts are not bonded to each other.

* * * * *